US012708778B2

(12) United States Patent
Grinberg et al.

(10) Patent No.: US 12,708,778 B2
(45) Date of Patent: Aug. 18, 2026

(54) SYNCHRONIZING RATE RESPONSES BETWEEN TWO CARDIAC PACEMAKERS

(71) Applicant: Medtronic, Inc., Minneapolis, MN (US)

(72) Inventors: Yanina Grinberg, Plymouth, MN (US); Kathryn E. Hilpisch, Cottage Grove, MN (US); Eric R. Williams, Maple Grove, MN (US); Hyun J. Yoon, Vadnais Heights, MN (US); Todd J. Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 581 days.

(21) Appl. No.: 17/814,182

(22) Filed: Jul. 21, 2022

(65) Prior Publication Data

US 2023/0053188 A1 Feb. 16, 2023

Related U.S. Application Data

(60) Provisional application No. 63/231,458, filed on Aug. 10, 2021.

(51) Int. Cl.

*A61N 1/365* (2006.01)
*A61B 5/00* (2006.01)
(Continued)

(52) U.S. Cl.

CPC ........ *A61N 1/36542* (2013.01); *A61B 5/1118* (2013.01); *A61B 5/7278* (2013.01); *A61B 2562/0219* (2013.01)

(58) Field of Classification Search

CPC ............ A61N 1/36542; A61N 1/37247; A61N 1/37288; A61B 5/1118; A61B 5/7278; A61B 2562/0219; A61B 5/686

See application file for complete search history.

(56) References Cited

U.S. PATENT DOCUMENTS

| | | | |
|---|---|---|---|
| 4,485,813 | A | 12/1984 | Anderson et al. |
| 5,024,222 | A | 6/1991 | Thacker |

(Continued)

FOREIGN PATENT DOCUMENTS

| | | | |
|---|---|---|---|
| EP | 3838335 | A1 | 6/2021 |
| WO | 2015191893 | A2 | 12/2015 |
| WO | 2016064662 | A1 | 4/2016 |

OTHER PUBLICATIONS

International Search Report and Written Opinion of International Application No. PCT/IB2022/057263 dated Oct. 19, 2022, 11 pp.

(Continued)

*Primary Examiner* — Brian T Gedeon

(74) *Attorney, Agent, or Firm* — Shumaker & Sieffert, P.A.

(57) ABSTRACT

A computing device may be communicably coupled to a first pacemaker implanted in a heart of a patient and a second pacemaker implanted in the heart of the patient. The computing device may receive, from the first pacemaker, first race responsive pacing data, and may receive, from the second pacemaker, second rate responsive pacing data. The computing device may synchronize, based at least in part on the first rate responsive pacing data and the second rate responsive pacing data, rate responsive pacing of the first pacemaker and the second pacemaker.

20 Claims, 5 Drawing Sheets

(51) Int. Cl.
*A61B 5/11* (2006.01)
*A61N 1/372* (2006.01)

(56) References Cited

U.S. PATENT DOCUMENTS

| | | | |
|---|---|---|---|
| 5,052,388 | A | 10/1991 | Sivula et al. |
| 5,507,782 | A | 4/1996 | Kieval et al. |
| 5,593,431 | A | 1/1997 | Sheldon |
| 5,885,471 | A | 3/1999 | Ruben et al. |
| 5,978,711 | A | 11/1999 | van Hove |
| 6,044,297 | A | 3/2000 | Sheldon et al. |
| 7,937,148 | B2 | 5/2011 | Jacobson |
| 8,433,409 | B2 | 4/2013 | Johnson et al. |
| 8,532,785 | B1 | 9/2013 | Crutchfield et al. |
| 8,541,131 | B2 | 9/2013 | Lund et al. |
| 9,522,280 | B2 | 12/2016 | Fischler et al. |
| 9,694,186 | B2 | 7/2017 | Carney et al. |
| 9,775,982 | B2 | 10/2017 | Grubac et al. |
| 9,802,055 | B2 | 10/2017 | Reinke et al. |
| 2012/0109236 | A1 | 5/2012 | Jacobson et al. |
| 2016/0015984 | A1 | 1/2016 | Demmer et al. |
| 2016/0310733 | A1* | 10/2016 | Sheldon ............... A61N 1/3756 |
| 2019/0308022 | A1 | 10/2019 | Demmer et al. |
| 2020/0368538 | A1 | 11/2020 | Min |
| 2020/0403717 | A1 | 12/2020 | Fishler et al. |

OTHER PUBLICATIONS

Steinwender et al., “Atrioventricular Synchronous Pacing Using a Leadless Ventricular Pacemaker: Results From the MARVEL 2 Study,” JACC: Clinical Electrophysiology, vol. 6, No. 1, Jan. 6, 2020, 13 pp.

* cited by examiner

SYNCHRONIZING RATE RESPONSES BETWEEN TWO CARDIAC PACEMAKERS

This application claims the benefit of U.S. Provisional Application Ser. No. 63/231,458, filed Aug. 10, 2021, which is entitled "SYNCHRONIZING RATE RESPONSES BETWEEN TWO CARDIAC PACEMAKERS" and is incorporated by reference herein in its entirety.

TECHNICAL FIELD

This disclosure generally relates to medical devices and, more particularly, synchronizing rate responses between two rate responsive cardiac pacemakers.

BACKGROUND

A rate responsive cardiac pacemaker may perform rate responsive cardiac pacing for a patient by changing its cardiac pacing rate based on changes in the activity level of the patient. In some instances, two or more rate responsive cardiac pacemakers may be implanted in the patient to each perform rate responsive cardiac pacing for the patient, e.g., for respective chambers of the heart of the patient, based on the activity level of the patient detected by each of the two or more rate responsive cardiac pacemakers.

SUMMARY

In accordance with the techniques of the disclosure, a medical device system is set forth herein that is able to accurately and seamlessly synchronize the pacing rate of two or more pacemakers that perform rate responsive cardiac pacing for a patient regardless of changes in the activity level of the patient. A computing device, such as a programmer, an external monitor, or a mobile device may receive rate responsive pacing data from each of the two or more pacemakers and may synchronize, based on the rate responsive pacing data from each of the two or more pacemakers, the rate responsive cardiac pacing of each of the two or more pacemakers. The techniques of this disclosure therefore enables multiple rate responsive pacemakers in a patient to perform cardiac pacing at the same pacing rate, thereby improving the comfort of the patient and reducing any potential negative medical outcomes from multiple pacemakers in the patient performing cardiac pacing at different rates.

A system of one or more computers and/or devices can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

In some aspects, the techniques described herein relate to a method including: receiving, by processing circuitry from a first pacemaker implanted in a heart of a patient, first rate responsive pacing data; receiving, by the processing circuitry from a second pacemaker implanted in the heart of the patient, second rate responsive pacing data; and synchronizing, by the processing circuitry and based at least in part on the first rate responsive pacing data and the second rate responsive pacing data, rate responsive pacing of the first pacemaker and the second pacemaker.

In some aspects, the techniques described herein relate to a medical device including: memory; and processing circuitry operably coupled to the memory and configured to: receive, from a first pacemaker implanted in a heart of a patient, first rate responsive pacing data; receive, from a second pacemaker implanted in the heart of the patient, second rate responsive pacing data; and synchronize, based at least in part on the first rate responsive pacing data and the second rate responsive pacing data, rate responsive pacing of the first pacemaker and the second pacemaker.

In some aspects, the techniques described herein relate to a non-transitory computer-readable medium including instructions that, when executed by processing circuitry of a medical device, cause the medical device to: receive, from a first pacemaker implanted in a heart of a patient, first rate responsive pacing data; receive, from a second pacemaker implanted in the heart of the patient, second rate responsive pacing data; and synchronize, based at least in part on the first rate responsive pacing data and the second rate responsive pacing data, rate responsive pacing of the first pacemaker and the second pacemaker.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF DRAWINGS

Like reference characters refer to like elements throughout the figures and description.

DETAILED DESCRIPTION

In general, aspects of this disclosure are directed to a medical device system that synchronizes the pacing rate of two or more pacemakers that perform rate responsive cardiac pacing for a patient regardless of changes in the activity level of the patient. A computing device, such as a programmer, an external monitor, or a mobile device may receive rate responsive pacing data from each of the two or more pacemakers and may synchronize, based on the rate responsive pacing data from each of the two or more pacemakers, the rate responsive cardiac pacing of each of the two or more pacemakers.

The computing device may synchronize, based on the rate responsive pacing data from each of the two or more pacemakers, the rate responsive cardiac pacing of each of the two or more pacemakers. By synchronizing the rate responsive cardiac pacing of each of the two or more pacemakers, the two or more pacemakers may perform cardiac pacing at similar rates as the activity level of the patient changes.

Each of the two or more pacemakers may perform rate responsive cardiac pacing using a respective rate response slope, which is a mapping of the activity level of a patient to the pacing rate of the respective pacemaker that correlates changes to the pacing rate of the respective pacemaker to changes in the activity level of the patient. In some examples, each of the two or more pacemakers may determine the activity level of the patient in the form of an activity count, which is a value that corresponds to the activity level of the patient, and the computing device may synchronize the rate responsive cardiac pacing of each of the two or more pacemakers by synchronizing the activity counts determined by each of the two or more pacemakers. That is, the two or more pacemakers may each, for a particular activity level of the patient, determine the same or similar activity count.

To synchronize the activity counts determined by each of the two or more pacemakers, the patient may undergo a triggered exercise test during which the two or more pacemakers may collect detailed information regarding the patient, such as the rate responsive pacing data. The computing device may thereby use such detailed information to synchronize the rate responsive cardiac pacing of the two or more pacemakers by matching the activity counts between each of the two or more pacemakers.

The techniques of this disclosure therefore enables multiple rate responsive pacemakers in a patient to perform cardiac pacing at the same pacing rate, thereby improving the comfort of the patient and reducing any potential negative medical outcomes from multiple pacemakers in the patient performing cardiac pacing at different rates.

Figure 1:
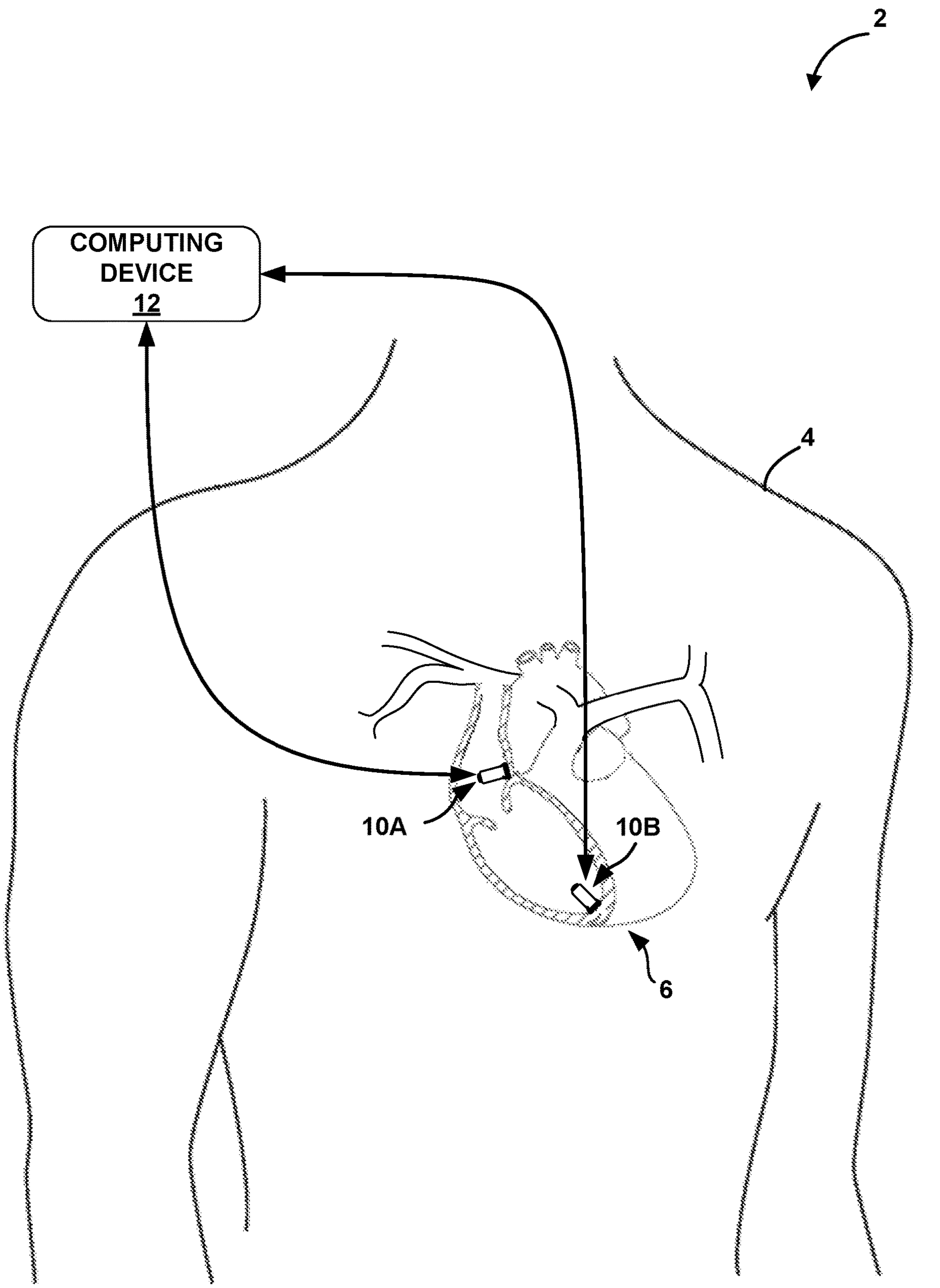
FIG. 1 illustrates the environment of an example of a medical device system in conjunction with a patient in accordance with the techniques of the disclosure.

FIG. 1 illustrates the environment of an example medical device system 2 in conjunction with a patient 4, in accordance with an apparatus and method of certain examples described herein. As shown in FIG. 1, medical device system 2 includes two or more rate responsive cardiac pacemakers, such as pacemaker 10A and pacemaker 10B, and one or more computing devices, such as computing device 12.

Each of pacemakers 10A and 10B (collectively "pacemakers 10") may be a leadless intracardiac cardiac pacemaker adapted for implantation within heart 6 of patient 4 that delivers electrical stimulation pulses to heart 6. Each of pacemakers 10A and 10B may be in wireless communication with computing device 12, as illustrated in FIG. 1. In some examples, pacemakers 10A and 10B may be implanted at different locations within heart 6. For example, pacemaker 10A may be an atrial intracardiac pacemaker implanted in an atrium of heart 6 (e.g., right atrium or left atrium) and pacemaker 10B may be a ventricular intracardiac pacemaker implanted in a ventricle in heart 6 (e.g., right ventricle or left ventricle).

Pacemakers 10A and 10B are each capable of producing electrical stimulation pulses, e.g., pacing pulses, delivered to heart 6 via one or more electrodes on the outer housing of pacemaker 10A and pacemaker 10B, respectively. Pacemakers 10A and 10B are rate responsive (also called rate modulated) cardiac pacemakers configured to adapt the pacing rate of pacemakers 10A and 10B to changes in patient 4's physical activity. Each of pacemakers 10A and 10B may include an activity sensor, such as an accelerometer or other motion sensor that measures patient 4's movement, and/or a respiration sensor, and may determine, based on patient 4's movement or other activity, the appropriate pacing rate for patient 4. As patient 4's activity level changes, the activity sensors of pacemakers 10A and 10B may be able to measure such changes in patient 4's activity level, and pacemakers 10A and 10B may, based on the changes in patient 4's activity level, adjust the pacing rate for patient 4.

Pacemakers 10A and 10B may each use a respective rate response slope, which may refer to any function relating activity level to pacing rate, to determine the pacing rate for a corresponding activity level of patient 4. A rate response slope for a rate responsive cardiac pacemaker, such as pacemaker 10A and pacemaker 10B, is a mapping of the activity level of patient 4 to the pacing rate of the pacemaker that correlates changes to the pacing rate of the pacemaker to changes in the activity level of patient 4. When pacemaker 10A detects an increase in patient 4's activity level, pacemaker 10A may use a rate response slope to determine whether and by how much to increase the pacing rate of pacemaker 10A. Similarly, when pacemaker 10A detects a decrease in patient 4's activity level, pacemaker 10A may use a rate response slope to determine whether and by how much to decrease the pacing rate of pacemaker 10A. In some examples, pacemakers 10A and 10B may periodically determine an activity level and then determine, based on the rate response slope, whether to change the pacing rate and to what value to change the pacing rate. Pacemakers 10A and 10B may each be associated with a separate rate response slope.

In some examples, a rate response slope, such as the rate response slope associated with pacemaker 10A and/or the rate response slope associated with pacemaker 10B, may be associated with a lower rate (LR) that indicates the minimum pacing rate and an upper rate (UR) that indicates the maximum pacing rate. A pacing rate between the LR and the UR on the rate response slope may be an adjusted daily living (ADL) rate, which is a pacing rate associated with a desired rate response during normal daily activities of patient 4, such as getting into and out of bed, walking around the house, and the like. The portion of the rate response slope between the UR and the ADL rate may be referred to as the ADL range, and the portion of the rate response slope between the ADL rate and the UR may be referred to as an exertion range. That is, the ADL range may include a range of pacing rates between the LR and the ADL rate, and the exertion range may include a range of pacing rates between the ADL rate and the UR rate. In some examples, the slope of the ADL range of the rate response slope may differ from the slope of the exertion range of the rate response slope, so that the rate response slope may actually include two rate response slopes: a first rate response slope in the ADL range and a second rate response slope in the exertion range.

In some examples, a rate response slope may include a rate response slope for increasing pacing rates and a rate response slope for decreasing pacing rates. When pacemaker 10A detects an increase in patient 4's activity level, pacemaker 10A may use an acceleration rate response slope for increasing pacing rates to determine whether and by how much to increase the pacing rate of pacemaker 10A. When pacemaker 10A detects a decrease in patient 4's activity level, pacemaker 10A may use a deceleration rate response slope for decreasing pacing rates to determine whether and by how much to decrease the pacing rate of pacemaker 10A.

In some examples, pacemakers 10A and 10B may each determine the activity level of patient 4 in the form of an activity count, which is a value that corresponds to the activity level of patient 4. Each of pacemakers 10A and 10B may determine the activity count for patient 4 based at least in part on the accelerometer signals outputted by the activity sensors of pacemakers 10A and 10B, such as determining the activity count for patient 4 based at least in part on the frequency and amplitude of one or more axis of the accelerometer signals outputted by the activity sensors of pacemakers 10A and 10B.

Computing device 12 may be a computing device configured for use in settings such as a home, clinic, or hospital, and may further be configured to communicate with pacemaker 10 via wireless telemetry. For example, computing device 12 may be coupled to a remote patient monitoring system, such as Carelink®, available from Medtronic Inc., of Minneapolis, Minn. Computing device 12 may, in some examples, comprise a programmer, an external monitor, or a mobile device, such as a mobile phone, a "smart" phone, a laptop, a tablet computer, a personal digital assistant (PDA), etc. In some examples, computing device 12 is a wearable electronic device, such as the SEEQ™ Mobile Cardiac Telemetry (MCT) system that was available from Medtronic, Inc., the AVIVO™ Mobile Patient Management (MPM) system that was available from Medtronic, Inc., a Holter monitor, or a type of wearable "smart" electronic apparel, such as a "smart" watch, "smart" patch, or "smart" glasses.

In some examples, a user, such as patient 4, a physician, technician, surgeon, electro-physiologist, or other clinician, may interact with computing device 12 to retrieve physiological or diagnostic information from pacemakers 10A and 10B. In some examples, a user, such as patient 4 or a clinician as described above, may also interact with computing device 12 to program pacemakers 10A and 10B, e.g., select or adjust values for operational parameters of pacemakers 10A and 10B. In some examples, computing device 12 acts as an access point to facilitate communication with pacemakers 10A and 10B. In some examples, computing device 12 may continually communicate with pacemakers 10A and 10B so that pacemakers 10A and 10B may continually send information sensed by pacemakers 10A and 10B, such as heart rate data of patient 4, cardiac electrogram data of patient 4, metrics of delivery of pacing or other therapies to patient 4, and the like to computing device 12.

Examples of communication techniques used by pacemakers 10A and 10B and computing device 12 include radiofrequency (RF) telemetry, which may be an RF link established via Bluetooth, Wi-Fi, or medical implant communication service (MICS). In some examples, computing device 12 may include a user interface configured to allow patient 4, a clinician, or another user to remotely interact with pacemakers 10A and 10B.

In some such examples, computing device 12, and/or any other device of medical device system 2, may be a wearable device (e.g., in the form of a necklace or other wearable item), that is operable to track the activity level of patient 4. Patient 4 may wear computing device 12 on or near patient 4's chest, such as via a necklace that hangs computing device 12 on or near patient 4's chest, via a strap that straps computing device 12 on or near patient 4's chest, and the like. Computing device 12 being worn by patient 4 so that computing device 12 is situated on or near patient 4's chest may enable computing device 12 to potentially track the activity level of patient 4 in ways that may better reflect the actual activity level of patient 4 compared with devices that may be worn on patient 4's periphery, such as on patient 4's legs or hands.

Additional examples of the one or more other implanted or computing devices may include an implanted, multi-channel cardiac pacemaker, ICD, IPG, leadless (e.g., intracardiac) pacemaker, extravascular pacemaker and/or ICD, or other IMD or combination of such IMDs configured to deliver CRT to heart 6, an external monitor, an external therapy delivery device such as an external pacing or electrical stimulation device, or a drug pump.

In accordance with the techniques of the disclosure, medical device system 2 may be configured to synchronize the rate response between pacemakers 10A and 10B, so that pacemakers 10A and 10B may perform cardiac pacing of heart 6 at similar rates as the activity level of patient 4 changes. Specifically, computing device 12 may communicate with pacemaker 10A and/or pacemaker 10B to program pacemaker 10A and/or pacemaker 10B to synchronize the rate response between pacemakers 10A and 10B to perform cardiac pacing at similar rates.

In some examples, synchronizing the rate response between pacemakers 10A and 10B may include synchronizing the rate response of pacemaker 10A in the ADL range with the rate response of pacemaker 10B in the ADL range and synchronizing the rate response of pacemaker 10A in the exertion range with the rate response of pacemaker 10B in the exertion range. In some examples, synchronizing the rate response between pacemakers 10A and 10B may include synchronizing the acceleration rate response scope of pacemaker 10A with the acceleration rate response scope of pacemaker 10B and synchronizing the deceleration rate response scope of pacemaker 10A with the deceleration rate response scope of pacemaker 10B.

Synchronize the rate response between pacemakers 10A and 10B, may not necessarily mean that pacemakers 10A and 10B each performs cardiac pacing of heart 6 at the same pacing rate at a given activity level of patient 4. In some examples, the rate response between pacemakers 10A and 10B may be synchronized such that, given an activity level of patient 4, pacemakers 10A and 10B may perform cardiac pacing at pacing rates that differ by no more than a specified amount of bpm or that differ by no more than a specified percentage. In some examples, the rate response between pacemakers 10A and 10B may be synchronized such that, given an activity level of patient 4, pacemakers 10A and 10B may perform cardiac pacing at pacing rates that differ by a fixed amount of bpm.

In some examples, the rate response between pacemakers 10A and 10B may be synchronized such that, given an activity level of patient 4, pacemakers 10A and 10B may perform cardiac pacing at pacing rates that differ by a first fixed amount of bpm when in the ADL range and that differ by a second fixed amount of bpm different from the first fix amount of bpm when in the exertion range.

In some examples, computing device 12 may be configured to synchronize the rate response between pacemakers 10A and 10B by synchronizing the activity counts determined by pacemakers 10A and 10B. Pacemakers 10A and 10B may each determine the activity level of patient 4 in the form of an activity count, which is a value that corresponds to the activity level of patient 4. Each of pacemakers 10A and 10B may determine the activity count for patient 4 based at least in part on the accelerometer signals outputted by the activity sensors of pacemakers 10A and 10B, such as determining the activity count for patient 4 based at least in part on the frequency and amplitude of the accelerometer signals outputted by the activity sensors of pacemakers 10A and 10B.

Because pacemakers 10A and 10B are disposed at different locations within heart 6 of patient 4, the activity sensors of pacemakers 10A and 10B may sense different amounts of movement, such as by sensing different levels of forces in different directions, as patient 4 moves, and may therefore generate accelerometer signals with different values. As such, when patient 4 is physically active, pacemakers 10A and 10B may not necessarily determine, at any point in time, the same activity counts. As such, computing device 12 may synchronize the rate response between pacemakers 10A and 10B by synchronizing the activity counts determined by pacemakers 10A and 10B. In some examples, pacemakers 10A and 10B may be able to communicate with each other within use of computing device 12 to synchronize the rate response between pacemakers 10A and 10B.

To synchronize the activity counts determined by pacemakers 10A and 10B, patient 4 may undergo a triggered exercise test that includes at least a period during which patient 4 performs moderate exercise and at least a period during which patient 4 is at rest. Such a triggered exercise test may be triggered by a clinician, and computing device 14 may send, to each of pacemakers 10A and 10B, an indication that a triggered exercise test is starting when the triggered exercise test begins and an indication that a triggered exercise test is ending when the triggered exercise test ends. During the triggered exercise test, each of pacemakers 10A and 10B may collect detailed information such as the activity counts, pacing rates, parameters of the activity sensors of pacemakers 10A and 10B, the accelerometer signals generated by the activity sensors of pacemakers 10A and 10B, and the like.

Computing device 12 may be configured to receive from pacemakers 10A and 10B the detailed information collected by pacemakers 10A and 10B and to synchronize the rate response between pacemaker 10A and pacemaker 10B based at least in part on the detailed information collected by pacemakers 10A and 10B during the triggered exercise test by matching the activity counts between pacemakers 10A and 10B. That is, given a set of activity counts generated by pacemaker 10A during the triggered exercise test and a set of activity counts generated by pacemaker 10B during the triggered exercise test, computing device 12 may be configured to modify the parameters of one or both of the activity sensors and/or the activity count algorithm used by one or both of pacemakers 10A and 10B to generate the activity counts so that the activity counts generated by pacemaker 10A during the triggered exercise test matches (e.g., differs by no more than a threshold value or percentage from) the activity counts generated by pacemaker 10B during the triggered exercise test.

In some examples, computing device 12 may be configured to modify parameters, such as the blanking period, the filter, and the gain of the activity sensor of pacemaker 10A, such that the activity sensor of pacemaker 10A would generate activity counts from the signals measured by pacemaker 10A during the triggered exercise test that match the activity counts generated by pacemaker 10B during the triggered exercise test. Computing device 12 may therefore be configured to program pacemaker 10A with the modified parameters of the activity sensor of pacemaker 10A and/or the modified activity count algorithm used by pacemaker 10A.

In some examples, computing device 12 may be configured to synchronize the rate response between pacemaker 10A and pacemaker 10B based at least in part on the detailed information collected by pacemakers 10A and 10B during the triggered exercise test by matching rate response slopes of pacemakers 10A and 10B during the triggered exercise test. To match the rate response slopes of pacemakers 10A and 10B, computing device 12 may modify the rate response of pacemaker 10A and/or pacemaker 10B so that the rate response slope of pacemaker 10A during the triggered exercise test matches (e.g., is the same as or within a threshold from) the rate response slope of pacemaker 10B during the triggered exercise test without modifying the activity counts generated by either pacemaker 10A or pacemaker 10B.

Pacemaker 10A and pacemaker 10B may each determine associations between activity counts and pacing rates, so that given an activity count value, a pacemaker may determine an associated pacing rate. Computing device 12 may therefore be configured to use the rate response slope of pacemaker 10B as a reference to modify the pacing rates associated with one or more activity counts for pacemaker 10A, thereby modifying the rate response slope of pacemaker 10A to match the rate response slope of pacemaker 10B. In this way, pacemaker 10A may use a rate response slope that matches the rate response slope of pacemaker 10B during the triggered exercise test.

In some examples, computing device 12 may be configured to modify associations between activity counts and pacing rates for pacemaker 10A as well as associations between activity counts and pacing rates for pacemaker 10B to achieve a specified target pacing rate given a specified activity level. For example, computing device 12 may be configured to modify the associations between activity counts and pacing rates for pacemaker 10A as well as the associations between activity counts and pacing rates for pacemaker 10B to achieve a target pacing rate of 100 beats per minute (bpm) when patient 4 is performing moderate exercise. Computing device 12 may therefore be configured to modify the associations between activity counts and pacing rates for pacemaker 10A to produce, given the activity counts generated by pacemaker 10A while patient 4 is performing moderate exercise, a targeted pacing rate (e.g., 100 bpm). Similarly, computing device 12 may be configured to modify associations between activity counts and pacing rates for pacemaker 10B to produce, given the activity counts generated by pacemaker 10B while patient 4 is performing moderate exercise, a targeted pacing rate (e.g., 100 bpm). Computing device 12 may therefore be configured to program pacemaker 10A and/or pacemaker 10B with the modified associations between activity counts and pacing rates.

In some examples, computing device 12 may be configured to modify the rate response slopes of pacemakers 10A and 10B to match the sensor rate histograms between pacemakers 10A and 10B. That is, computing device 12 may be configured to modify the rate response algorithm of pacemaker 10A and/or pacemaker 10 to generate, for a given time period, the same or similar (e.g., within a specified percentage) distribution of pacing rates by pacemakers 10A and 10B. A sensor rate histogram for a pacemaker is a graph that illustrates range distributions of the pacing rate of the pacemaker. Computing device 12 may be configured to, at a follow-up clinical visit by patient 4, download or otherwise receive sensor rate data from pacemakers 10A and 10B. Such sensor rate data may be data sensed and stored by pacemakers 10A and 10B since the previous follow-up. Computing device 12 may be configured to collate or otherwise process the sensor rate data from pacemakers 10A and 10B to determine a sensor rate histogram for pacemaker 10A indicative of the distribution of pacing rates by pacemaker 10A during the period since the last follow-up clinical visit and a sensor rate histogram for 10B indicative of the distribution of pacing rates by pacemaker 10*b* during the period since the last follow-up clinical visit.

Computing device 12 may be configured to receive sensor rate data from pacemaker 10A and to determine, based on the sensor rate data from pacemaker 10A, a sensor rate histogram for pacemaker 10A. Similarly, computing device 12 may be configured to receive sensor rate data from pacemaker 10B and to determine, based on the sensor rate data from pacemaker 10B, a sensor rate histogram for pacemaker 10B. Sensor rate data received from pacemakers 10A and 10B may be information regarding the pacing rates of each of pacemakers 10A and 10B over time since the last follow-up clinical visit by patient 4, the activity counts associated with the pacing rates of each of pacemakers 10A and 10B over time since the last follow-up clinical visit by patient 4, and the like.

Computing device 12 may be configured to modify the rate response slope of at least one of pacemaker 10A and pacemaker 10B so that the sensor rate histogram of pacemaker 10A matches (e.g., is the same as) the sensor rate histogram of pacemaker 10B. In some examples, computing device 12 may be configured to modify rate response slope of pacemaker 10A by modifying or determining a rate response algorithm for pacemaker 10A, such that the rate response algorithm is usable by pacemaker 10A to generate, based on the activity counts associated with the pacing rates of pacemakers 10A since the last follow-up clinical visit by patient 4, associated pacing rates having distribution that matches the distribution of pacing rates of pacemaker 10B over time since the last follow-up clinical visit by patient 4, which corresponds to the second sensor rate histogram. Computing device 12 may therefore cause pacemaker 10A to use the determined rate response algorithm for determining pacing rates based on activity counts, such as by programming pacemaker 10A to use the determined rate response algorithm, sending an indication of the determined rate response slope to pacemaker 10A, and the like.

In examples where each of the rate response slopes of pacemakers 10A and 10B may be in an ADL range and an exertion range, computing device 12 may be configured to separately modify the rate response slope of pacemaker 10A in the ADL range and the portion of the rate response slope of pacemaker 10A in the exertion range so that the rate response slope of pacemaker 10A in the ADL range matches the rate response slope of pacemaker 10B in the ADL range and the rate response slope of pacemaker 10A in the exertion range matches the rate response slope of pacemaker 10B in the exertion range. For example, computing device 12 may be configured to modify or determine a first rate response algorithm that is usable by pacemaker 10A to generate associated pacing rates in the ADL range having a distribution that matches the distribution of pacing rates in the ADL range of pacemaker 10B. Computing device 12 may also be configured to modify or determine a second rate response algorithm different from the first rate response algorithm that is usable by pacemaker 10A to generate associated pacing rates in the exertion range having a distribution that matches the distribution of exertion rates in the ADL range of pacemaker 10B.

In some examples, computing device 12 may be configured to modify the rate response slopes of pacemakers 10A and 10B to match the activity count histograms between pacemakers 10A and 10B. That is, computing device 12 may be configured to modify the rate response algorithm of pacemaker 10A and/or pacemaker 10 to generate, for a given time period, the same or similar (e.g., within a specified percentage) distribution of activity counts by pacemakers 10A and 10B. An activity count histogram for a pacemaker is a graph that illustrates range distributions of the activity counts of the pacemaker.

Computing device 12 may be configured to, at a follow-up clinical visit by patient 4, download receive, or otherwise determine activity counts from the data produced by pacemakers 10A and 10B since the previous follow-up. For example, activity counts may be determined based on the accelerometer signals outputted by the activity sensors of pacemakers 10A and 10B. Computing device 12 may be configured to collate or otherwise process the activity counts from each of pacemakers 10A and 10B to determine an activity count histogram for pacemaker 10A indicative of the distribution of activity counts determined by pacemaker 10A during the period since the last follow-up clinical visit and an activity counts histogram for 10B indicative of the distribution of activity counts determined by pacemaker 10*b* during the period since the last follow-up clinical visit.

Computing device 12 may be configured to modify the rate response slope of at least one of pacemaker 10A and pacemaker 10B so that the activity count histogram of pacemaker 10A matches (e.g., is the same as or is within a specified percentage of) the activity count histogram of pacemaker 10B. In some examples, computing device 12 may be configured to modify rate response slope of pacemaker 10A by modifying or determining a rate response algorithm for pacemaker 10A, such that the rate response algorithm is usable by pacemaker 10A to generate a distribution of activity counts that matches the distribution of the activity counts of pacemaker 10B over time since the last follow-up clinical visit by patient 4, which corresponds to the second activity count histogram. Computing device 12 may therefore cause pacemaker 10A to use the determined rate response algorithm for determining pacing rates based on activity counts, such as by programming pacemaker 10A to use the determined rate response algorithm, sending an indication of the determined rate response slope to pacemaker 10A, and the like.

In examples where each of the rate response slopes of pacemakers 10A and 10B may be in an ADL range and an exertion range, computing device 12 may be configured to separately modify the rate response slope of pacemaker 10A in the ADL range and the portion of the rate response slope of pacemaker 10A in the exertion range so that the rate response slope of pacemaker 10A in the ADL range matches the rate response slope of pacemaker 10B in the ADL range and the rate response slope of pacemaker 10A in the exertion range matches the rate response slope of pacemaker 10B in the exertion range. For example, computing device 12 may be configured to modify or determine a first rate response algorithm that is usable by pacemaker 10A to determine pacing rates in the ADL range having a distribution of activity counts that matches the distribution of pacing rates in the ADL range of pacemaker 10B. Computing device 12 may also be configured to modify or determine a second rate response algorithm different from the first rate response algorithm that is usable by pacemaker 10A to determine associated pacing rates in the exertion range having a distribution of activity counts that matches the distribution of exertion rates in the ADL range of pacemaker 10B. The techniques of the disclosure may provide specific improvements to the field of rate responsive cardiac pacing by cardiac pacemakers such as pacemakers 10A and 10B. For example, the techniques of the disclosure may ensure that two different pacemakers implanted in a patient perform cardiac pacing at the same rate, thereby potentially improving patient comfort and reducing any potential patient discomfort from mismatches in the cardiac pacing rate of pacemakers implanted in the patient.

Figure 2:
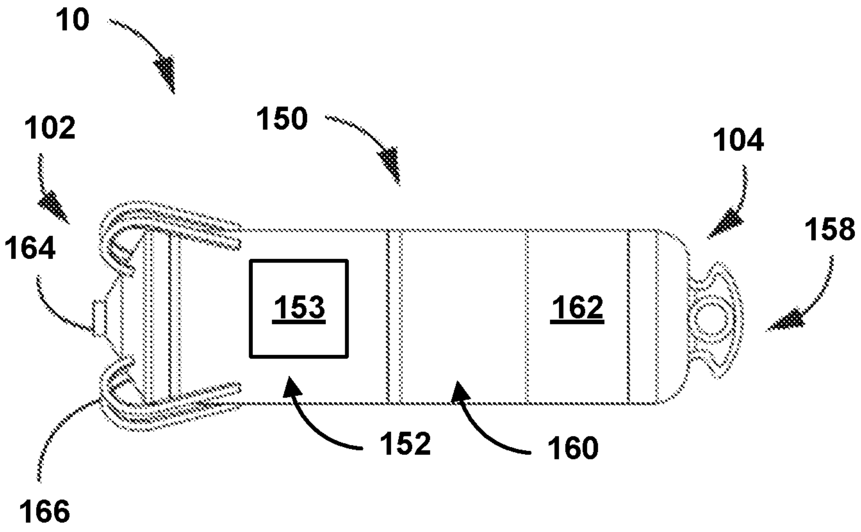
FIG. 2 is a block diagram illustrating an example of the rate responsive pacemaker of FIG. 1.

FIG. 2 is a conceptual diagram illustrating an example of a rate responsive pacemaker in accordance with the techniques of the disclosure. As shown in FIG. 2, pacemaker 10 is an example of pacemaker 10A and pacemaker 10B of FIG.

1. Pacemaker 10 includes electrodes 162 and 164 spaced apart along the housing 150 of pacemaker 10 for sensing electrogram data from heart 6 of FIG. 1 and delivering pacing pulses to heart 6. Electrode 164 is shown as a tip electrode extending from a distal end 102 of pacemaker 10, and electrode 162 is shown as a ring electrode along a mid-portion of housing 150, for example adjacent proximal end 104. Distal end 102 is referred to as "distal" in that it is expected to be the leading end as pacemaker 10 is advanced through a delivery tool, such as a catheter, and placed against a targeted pacing site.

Electrodes 162 and 164 form an anode and cathode pair for bipolar cardiac pacing and sensing. In alternative embodiments, pacemaker 10 may include two or more ring electrodes, two tip electrodes, and/or other types of electrodes exposed along pacemaker housing 150 for delivering electrical stimulation to heart 6 and sensing electrogram data. Electrodes 162 and 164 may be, without limitation, titanium, platinum, iridium or alloys thereof and may include a low polarizing coating, such as titanium nitride, iridium oxide, ruthenium oxide, platinum black, among others. Electrodes 162 and 164 may be positioned at locations along pacemaker 10 other than the locations shown.

Housing 150 is formed from a biocompatible material, such as a stainless steel or titanium alloy. In some examples, the housing 150 may include an insulating coating. Examples of insulating coatings include parylene, urethane, PEEK, or polyimide, among others. The entirety of the housing 150 may be insulated, but only electrodes 162 and 164 uninsulated. In the illustrated example, electrode 162 may be an uninsulated portion of an electrically conductive part of housing 150, and electrode 164 may be conductive element disposed within an insulative part of housing 150. Electrode 164 may serve as a cathode electrode and be coupled to internal circuitry, e.g., a pacing pulse generation circuit and electrogram sensing circuitry, enclosed by housing 150 via an electrical feedthrough crossing housing 150. Electrode 162 may be formed to define a ring electrode as generally shown in FIG. 2. In other examples, the entire periphery of the housing 150 may function as an electrode that is electrically isolated from tip electrode 164, instead of providing a localized ring electrode such as anode electrode 162. Electrode 162 formed along an electrically conductive portion of housing 150 serves as a return anode during pacing and sensing.

The housing 150 includes a control electronics subassembly 152, which houses the electronics 153 for sensing cardiac signals, producing pacing pulses and controlling therapy delivery and other functions of pacemaker 10. Pacemaker 10 may further include an activity sensor, which may be implemented, e.g., as a multi-axial accelerometer enclosed within housing 150. The accelerometer provides a signal to a processor included in control electronics subassembly 152 for signal processing and analysis for generating accelerometer signals that pacemaker 10 may be configured to use to generate activity counts, and pacemaker 10 may be configured to use a rate response algorithm to determine, based on the activity counts, pacing rates.

Housing 150 further includes a battery subassembly 160, which provides power to the electronics 153. Additional description of batteries implemented by battery subassembly 160 may be found in U.S. Pat. No. 8,433,409 to Johnson, et al., entitled "Implantable medical device battery," filed on Jan. 29, 2019, and issued on Apr. 30, 2013 and in U.S. Pat. No. 8,541,131 to Lund, et al., entitled "Elongate battery for implantable medical device," filed on Aug. 28, 2009, and issued on Sep. 24, 2013, the entire contents of each of which are incorporated herein by reference.

Pacemaker 10 may include a set of fixation tines 166 to secure pacemaker 10 to patient tissue, e.g., by actively engaging with the atrial or ventricular endocardium. Fixation tines 166 are configured to anchor pacemaker 10 to position electrode 164 in operative proximity to a targeted tissue for delivering therapeutic electrical stimulation pulses. Numerous types of active and/or passive fixation members may be employed for anchoring or stabilizing pacemaker 10 in an implant position. Additional detail with respect to fixation tines 166 may be found in U.S. Pat. No. 9,775,982 to Grubac, et al., entitled "Implantable medical device fixation," filed on Apr. 28, 2011 and issued on Oct. 3, 201, the entire content of which is incorporated herein by reference.

Pacemaker 10 may optionally include a delivery tool interface 158. Delivery tool interface 158 may be located at the proximal end 104 of pacemaker 10 and is configured to connect to a delivery device, such as a catheter, used to position pacemaker 10 at an implant location during an implantation procedure, for example within a heart chamber.

Figure 3:
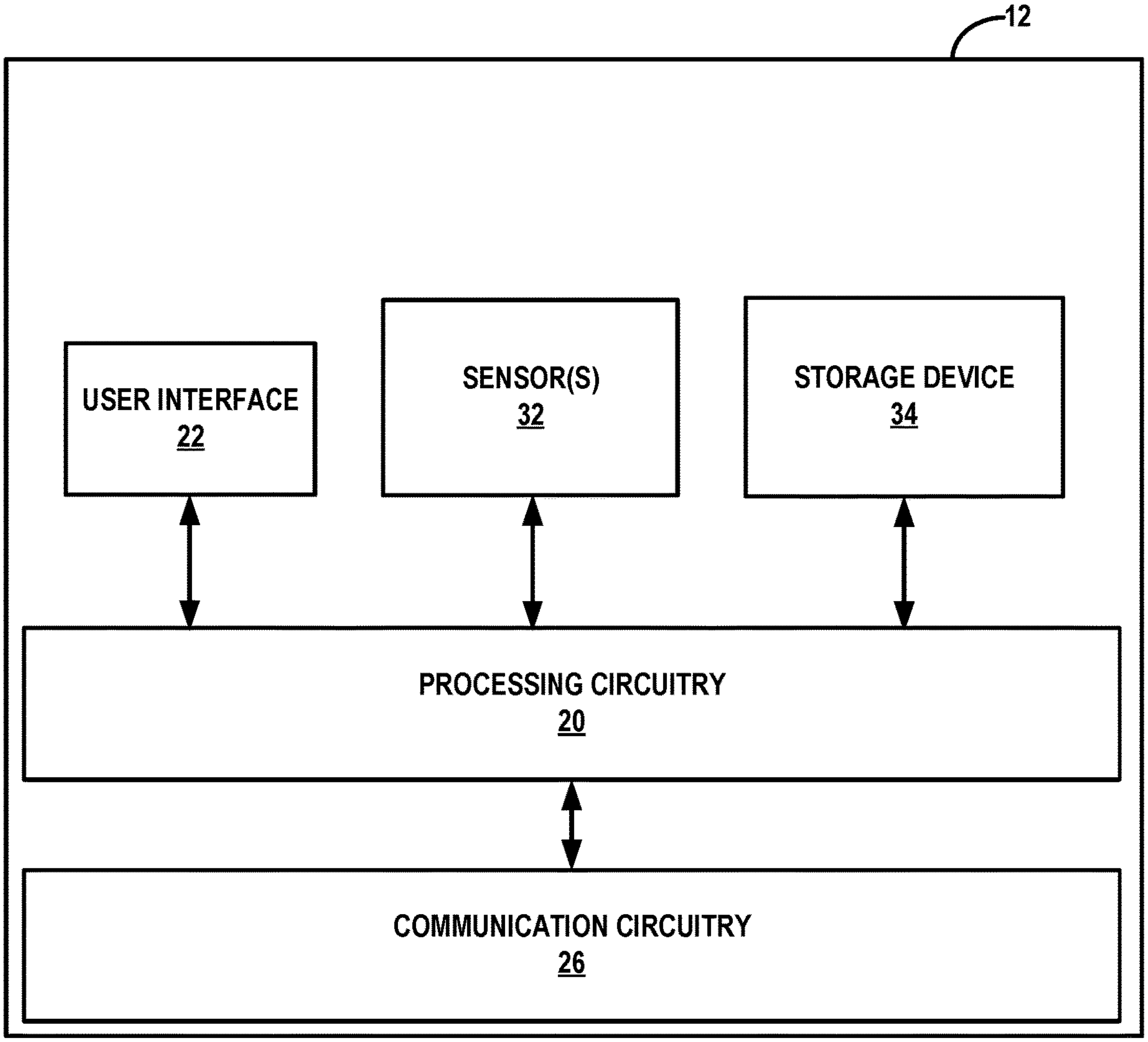
FIG. 3 is a block diagram illustrating an example configuration of the computing device of FIG. 1.

FIG. 3 is a block diagram illustrating an example configuration of computing device 12 of FIG. 1. In the example of FIG. 3, the at least one computing device 12 includes processing circuitry 20, communication circuitry 26, one or more sensors 32, storage device 34, and user interface device 22.

Processing circuitry 20 may include one or more processors that are configured to implement functionality and/or process instructions for execution within computing device 12. For example, processing circuitry 20 may be capable of processing instructions stored in storage device 34. Processing circuitry 20 may include, for example, microprocessors, a digital signal processors (DSPs), an application specific integrated circuits (ASICs), field-programmable gate arrays (FPGAs), complex programmable logic devices (CPLDs), or equivalent integrated or discrete logic circuitry, or a combination of any of the foregoing devices or circuitry. Accordingly, processing circuitry 20 may include any suitable structure, whether in hardware, software, firmware, or any combination thereof, to perform the functions ascribed herein to processing circuitry 20.

User interface device 22 includes a display (not shown), such as a liquid crystal display (LCD) or a light emitting diode (LED) display or other type of screen, with which processing circuitry 20 may present health- or device-related information, e.g., cardiac EGMs. In addition, user interface device 22 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interface device 22 presented by processing circuitry 20 of computing device 12 and provide input.

Communication circuitry 26 may include any suitable hardware, firmware, software or any combination thereof for communicating with another device, such as pacemakers 10. Under the control of processing circuitry 20, communication circuitry 26 may receive downlink telemetry from, as well as send uplink telemetry to, pacemakers 10, or another device. Communication circuitry 26 may be configured to transmit or receive signals via inductive coupling, electromagnetic coupling, NFC, RF communication, Bluetooth®, Wi-Fi™, or other proprietary or non-proprietary wireless communication schemes. Communication circuitry 26 may also be configured to communicate with devices other than pacemakers 10 via any of a variety of forms of wired and/or wireless communication and/or network protocols.

Data exchanged between computing device 12 and pacemakers 10 may include operational parameters of pacemakers 10. Computing device 12 may transmit data, including computer-readable instructions, to pacemakers 10. Pacemakers 10 may receive and implement the computer-readable instructions. In some examples, the computer-readable instructions, when implemented by pacemakers 10, may control pacemakers 10 to change one or more operational parameters, export collected data, etc.

One or more sensors 32 may be configured to sense, measure, and/or collect information regarding computing device 12 and/or patient 4. Storage device 34 may be configured to store information within computing device 12 during operation. Storage device 34 may include a computer-readable storage medium or computer-readable storage device. In some examples, storage device 34 includes one or more of a short-term memory or a long-term memory. Storage device 34 may include, for example, read-only memory (ROM), random access memory (RAM), non-volatile RAM (NVRAM), Dynamic RAM (DRAM), Static RAM (SRAM), magnetic discs, optical discs, flash memory, forms of electrically-erasable programmable ROM (EEPROM) or erasable programmable ROM (EPROM), or any other digital media. In some examples, storage device 34 is used to store data indicative of instructions for execution by processing circuitry 20. Storage device 34 may also be used to store data as a result of operations performed by processing circuitry 20.

Processing circuitry 20 may be configured to communicate, via communication circuitry 26, with pacemakers 10A and 10B implanted in heart 6 of patient 4 to synchronize the rate response pacing of pacemakers 10A and 10B, such that pacemakers 10A and 10B may perform cardiac pacing of heart 6 at similar rates. In some examples, processing circuitry 20 may be configured to synchronize the rate response between pacemakers 10A and 10B by synchronizing the activity counts determined by pacemakers 10A and 10B. Pacemakers 10A and 10B may each determine the activity level of patient 4 in the form of an activity count, which is a value that corresponds to the activity level of patient 4.

Synchronizing the rate response pacing of pacemakers 10A and 10B do not necessarily mean that pacemakers 10A and 10B perform cardiac pacing of heart 6 at the same pacing rates. In some examples, synchronizing the rate response pacing of pacemakers 10A and 10B may cause pacemakers 10A and 10B to perform cardiac pacing of heart 6 at a pacing rate that differs by no more than a threshold value or a threshold percentage. In some examples, synchronizing the rate response pacing of pacemakers 10A and 10B may cause pacemakers 10A and 10B to perform cardiac pacing of heart 6 at pacing rates that differs by a fixed pacing rate, such as a fixed difference in bpm.

In some examples, synchronizing rate response pacing of pacemakers 10A and 10B may cause the difference between the pacing rates of pacemakers 10A and 10B to change when in different pacing rate ranges. For example, synchronizing the rate response pacing of pacemakers 10A and 10B may cause pacemakers 10A and 10B to perform cardiac pacing of heart 6 at pacing rates that differs by a first fixed value when the pacing rates are between the lower rate and the adjusted daily living rate, and to perform cardiac pacing of heart 6 at pacing rates that differs by a second fixed value different from the first fixed value when the pacing rates are between the adjusted daily living rate and the upper rate.

To synchronize the activity counts determined by pacemakers 10A and 10B, patient 4 may undergo a triggered exercise test that includes at least a period during which patient 4 performs moderate exercise and at least a period during which patient 4 is at rest. During the triggered exercise test, each of pacemakers 10A and 10B may collect rate responsive pacing data, which may be detailed information such as the activity counts, pacing rates, parameters of the activity sensors of pacemakers 10A and 10B, the accelerometer signals generated by the activity sensors of pacemakers 10A and 10B, and the like.

Processing circuitry 20 may be configured to receive, from pacemakers 10A and 10B, the rate responsive pacing data collected by pacemakers 10A and 10B and to synchronize the rate response between pacemaker 10A and pacemaker 10B based at least in part on the rate responsive pacing data collected by pacemakers 10A and 10B during the triggered exercise test by matching the activity counts between pacemakers 10A and 10B. In some examples, given a set of activity counts generated by pacemaker 10A during the triggered exercise test and a set of activity counts generated by pacemaker 10B during the triggered exercise test, processing circuitry 20 may be configured to modify the parameters of one or both of the activity sensors and/or the activity count algorithm used by one or both of pacemakers 10A and 10B to generate the activity counts so that the activity counts generated by pacemaker 10A during the triggered exercise test matches the activity counts generated by pacemaker 10B during the triggered exercise test.

In some examples, processing circuitry 20 may be configured to modify parameters such as the blanking period, the filter, and the gain of the activity sensor of pacemaker 10A to generate activity counts from the signals measured by pacemaker 10A during the triggered exercise test that matches the activity counts generated by pacemaker 10B during the triggered exercise test. Computing device 12 may therefore be configured to program pacemaker 10A with the modified parameters of the activity sensor of pacemaker 10A and/or the modified activity count algorithm used by pacemaker 10A.

In some examples, processing circuitry 20 may be configured to synchronize the rate response between pacemaker 10A and pacemaker 10B based at least in part on the rate responsive pacing data collected by pacemakers 10A and 10B during the triggered exercise test by matching rate response slopes of pacemakers 10A and 10B during the triggered exercise test. To match the rate response slopes of pacemakers 10A and 10B, computing device 12 may modify the rate responsive algorithm(s) of pacemaker 10A and/or pacemaker 10B so that the rate response slope of pacemaker 10A during the triggered exercise test matches (e.g., is the same as) the rate response slope of pacemaker 10B during the triggered exercise test without modifying the activity counts generated by either pacemaker 10A or pacemaker 10B.

Pacemaker 10A and pacemaker 10B may each use a rate response algorithm to determine, given an activity count, a pacing rate. Computing device 12 may therefore be configured to use the rate response slope of pacemaker 10B as a reference to modify a rate response algorithm of pacemaker 10A, so that pacemaker 10A may generate, based on the modified rate response algorithm, a rate response slope from the activity counts of pacemaker 10A during the triggered exercise test that matches the rate response slope of pacemaker 10B during the triggered exercise test.

In some examples, when the rate response slope includes a rate response slope in the ADL range and a rate response slope in the exertion range, computing device 12 may be configured to modify a rate response algorithm of pacemaker 10A associated with the rate response slope in the ADL range and to modify a rate response algorithm of pacemaker 10A associated with the rate response slope in the exertion range. Pacemaker 10A may generate, based on the modified response algorithm associated with the rate response slope in the ADL range, a rate response slope in the ADL range from the activity counts of pacemaker 10A during the triggered exercise test that matches the rate response slope of pacemaker 10B in the ADL range during the triggered exercise test. Similarly, pacemaker 10A may generate, based on the modified response algorithm associated with the rate response slope in the exertion range, a rate response slope in the exertion range from the activity counts of pacemaker 10A during the triggered exercise test that matches the rate response slope of pacemaker 10B in the exertion range during the triggered exercise test.

In some examples, processing circuitry 20 may be configured to modify the rate response algorithm of pacemaker 10A as well as the rate response algorithm of pacemaker 10B to achieve a specified target pacing rate given a specified activity level. For example, processing circuitry 20 may be configured to modify the rate response algorithm of pacemaker 10A as well as the rate response algorithm of pacemaker 10B to achieve a target pacing rate of 100 beats per minute (bpm) when patient 4 is performing moderate exercise. Computing device 12 may therefore be configured to modify the rate response algorithm of pacemaker 10A to produce, given the activity counts generated by pacemaker 10A while patient 4 is performing moderate exercise, a targeted pacing rate (e.g., 100 bpm). Similarly, processing circuitry 20 may be configured to modify the rate response algorithm of pacemaker 10B to produce, given the activity counts generated by pacemaker 10B while patient 4 is performing moderate exercise, a targeted pacing rate (e.g., 100 bpm). Computing device 12 may therefore be configured to program pacemaker 10A and/or pacemaker 10B with the modified rate response algorithm.

In some examples, processing circuitry 20 may be configured to modify the rate response slopes of pacemakers 10A and 10B to match the sensor rate histograms between pacemakers 10A and 10B. That is, processing circuitry 20 may be configured to modify the rate response algorithm of pacemaker 10A and/or pacemaker 10 to generate, for a given time period, the same distribution of pacing rates by pacemakers 10A and 10B. A sensor rate histogram for a pacemaker is a graph that illustrates range distributions of the pacing rate of the pacemaker. Processing circuitry 20 may be configured to, at a follow-up clinical visit by patient 4, download or otherwise receive sensor rate data from pacemakers 10A and 10B. Such sensor rate data may be data sensed and stored by pacemakers 10A and 10B since the previous follow-up. Processing circuitry 20 may be configured to collate or otherwise process the sensor rate data from pacemakers 10A and 10B to determine a sensor rate histogram for pacemaker 10A indicative of the distribution of pacing rates by pacemaker 10A during the period since the last follow-up clinical visit and a sensor rate histogram for 10B indicative of the distribution of pacing rates by pacemaker 10*b* during the period since the last follow-up clinical visit.

Processing circuitry 20 may be configured to receive sensor rate data from pacemaker 10A and to determine, based on the sensor rate data from pacemaker 10A, a sensor rate histogram for pacemaker 10A. Similarly, processing circuitry 20 may be configured to receive sensor rate data from pacemaker 10B and to determine, based on the sensor rate data from pacemaker 10B, a sensor rate histogram for pacemaker 10B. Sensor rate data received from pacemakers 10A and 10B may be information regarding the pacing rates of each of pacemakers 10A and 10B over time since the last follow-up clinical visit by patient 4, the activity counts associated with the pacing rates of each of pacemakers 10A and 10B over time since the last follow-up clinical visit by patient 4, and the like.

Processing circuitry 20 may be configured to modify the rate response slope of at least one of pacemaker 10A and pacemaker 10B so that the sensor rate histogram of pacemaker 10A matches (e.g., is the same as) the sensor rate histogram of pacemaker 10B. In some examples, processing circuitry 20 may be configured to modify rate response slope of pacemaker 10A by modifying or determining a rate response algorithm for pacemaker 10A, such that the rate response algorithm is usable by pacemaker 10A to generate, based on the activity counts associated with the pacing rates of pacemakers 10A since the last follow-up clinical visit by patient 4, associated pacing rates having distribution that matches the distribution of pacing rates of pacemaker 10B over time since the last follow-up clinical visit by patient 4, which corresponds to the second sensor rate histogram. Computing device 12 may therefore cause pacemaker 10A to use the determined rate response algorithm for determining pacing rates based on activity counts, such as by programming pacemaker 10A to use the determined rate response algorithm, sending an indication of the determined rate response slope to pacemaker 10A, and the like.

In some examples, processing circuitry 20 may be configured to modify the rate response slopes of pacemakers 10A and 10B to match the activity count histograms between pacemakers 10A and 10B. That is, processing circuitry 20 may be configured to modify the rate response algorithm of pacemaker 10A and/or pacemaker 10 to generate, for a given time period, the same distribution of activity by pacemakers 10A and 10B. An activity count histogram for a pacemaker is a graph that illustrates range distributions of the activity counts of the pacemaker. Processing circuitry 20 may be configured to, at a follow-up clinical visit by patient 4, download or otherwise receive sensor rate data from pacemakers 10A and 10B. Such sensor rate data may be data sensed and stored by pacemakers 10A and 10B since the previous follow-up. Processing circuitry 20 may be configured to collate or otherwise process the sensor rate data from pacemakers 10A and 10B to determine an activity histogram for pacemaker 10A indicative of the distribution of activity counts by pacemaker 10A during the period since the last follow-up clinical visit and an activity count histogram for 10B indicative of the distribution of activity counts by pacemaker 10*b* during the period since the last follow-up clinical visit.

Processing circuitry 20 may be configured to receive sensor rate data from pacemaker 10A and to determine, based on the sensor rate data from pacemaker 10A, an activity count histogram for pacemaker 10A. Similarly, processing circuitry 20 may be configured to receive sensor rate data from pacemaker 10B and to determine, based on the sensor rate data from pacemaker 10B, an activity count histogram for pacemaker 10B. Sensor rate data received from pacemakers 10A and 10B may be information regarding the pacing rates of each of pacemakers 10A and 10B over time since the last follow-up clinical visit by patient 4, the activity counts associated with the pacing rates of each of pacemakers 10A and 10B over time since the last follow-up clinical visit by patient 4, and the like.

Processing circuitry 20 may be configured to modify the rate response slope of at least one of pacemaker 10A and pacemaker 10B so that the activity count histogram of pacemaker 10A matches (e.g., is the same as) the activity count histogram of pacemaker 10B. In some examples, processing circuitry 20 may be configured to modify rate response slope of pacemaker 10A by modifying or determining a rate response algorithm for pacemaker 10A, such that the rate response algorithm is usable by pacemaker 10A to generate, based on the activity counts associated with the pacing rates of pacemakers 10A since the last follow-up clinical visit by patient 4, associated activity counts having distribution that matches the distribution of pacing rates of pacemaker 10B over time since the last follow-up clinical visit by patient 4, which corresponds to the second activity count histogram. Computing device 12 may therefore cause pacemaker 10A to use the determined rate response algorithm for determining pacing rates based on activity counts, such as by programming pacemaker 10A to use the determined rate response algorithm, sending an indication of the determined rate response slope to pacemaker 10A, and the like.

Figure 4:
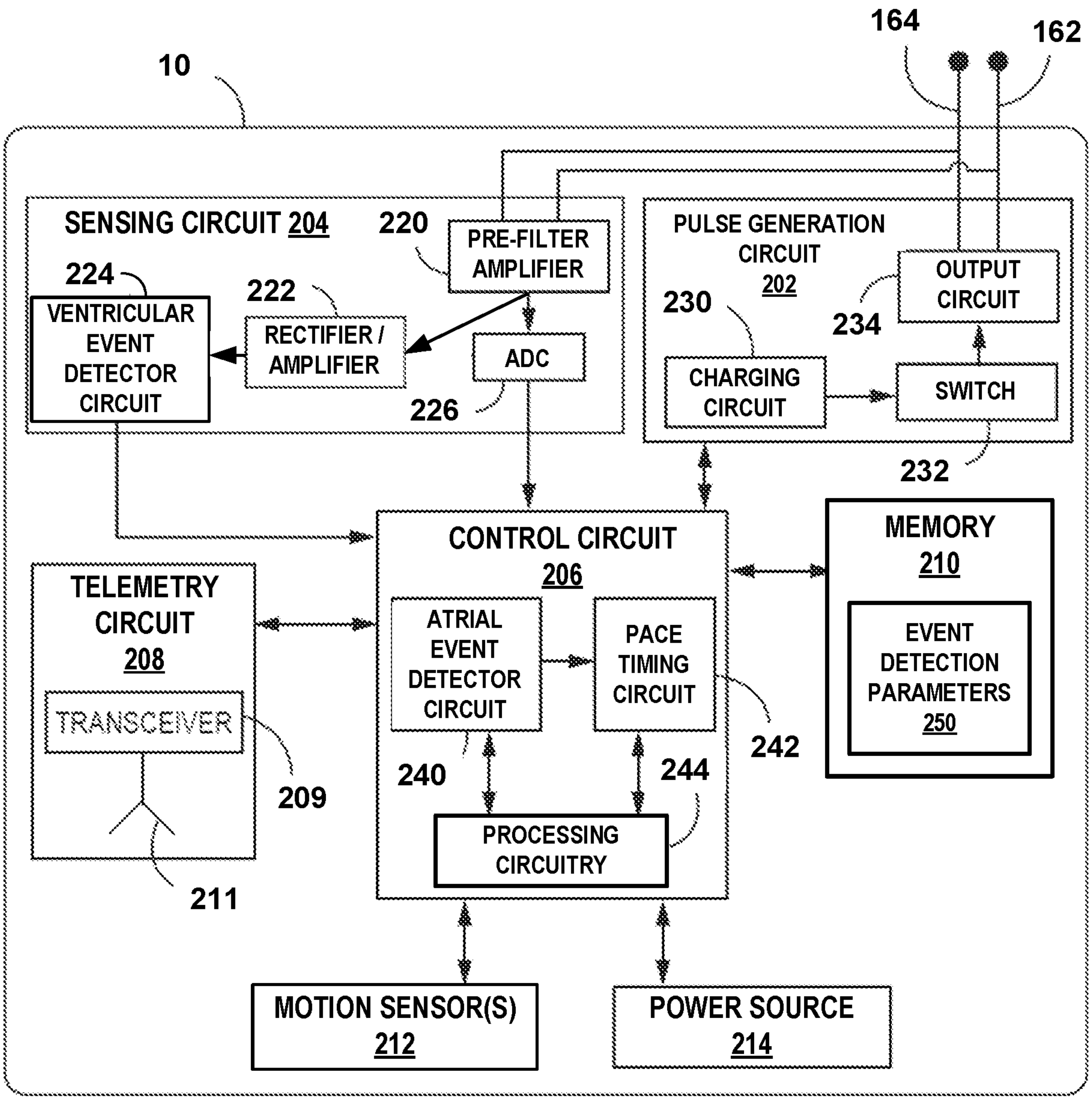
FIG. 4 is a block diagram of an example configuration of pacemaker of FIG. 2 in accordance with the techniques of the disclosure.

FIG. 4 is a block diagram of an example configuration of pacemaker 10 of FIG. 2 in accordance with the techniques of the disclosure. Pacemaker 10 includes a pulse generation circuit 202, a sensing circuit 204, a control circuit 206, memory 210, telemetry circuit 208, motion sensor 212 and a power source 214.

Motion sensor 212, also referred to throughout this disclosure as an activity sensor, may be a multi-axis sensor, e.g., a two-dimensional or three-dimensional sensor, with each axis providing a signal that may be analyzed individually or in combination for detecting cardiac mechanical events. In the example of FIG. 4, motion sensor 212 is implemented as an accelerometer and may also be referred to herein as "accelerometer 212." However, in other examples, motion sensor 212 is another type of motion sensor or mechanical sensor capable of detecting mechanical motion of heart 6, such as a piezoelectric sensor or a MEMS device. Motion sensor 212 produces an electrical signal correlated to mechanical motion or vibration of sensor 212 (and pacemaker 10), e.g., when subjected to flowing blood and cardiac motion. The motion sensor 212 may include, e.g., filters, amplifiers, rectifiers, an ADC and/or other components for producing a mechanical motion signal passed to control circuit 206. For example, each vector signal corresponding to each individual axis of a multi-axis accelerometer may be filtered by a high pass filter, e.g., a 10 Hz high pass filter, and rectified for use by atrial event detector circuit 240 for detecting atrial systolic events. The high pass filter may be lowered (e.g., to 5 Hz) if needed to detect atrial signals that have lower frequency content. In some examples, high pass filtering is performed with no low pass filtering. In other examples, each accelerometer axis signal is filtered by a low pass filter, e.g., a 30 Hz low pass filter, with or without high pass filtering.

Motion sensor 212 may be a one-dimensional, single axis accelerometer, two-dimensional or three-dimensional multi-axis accelerometer. One example of an accelerometer for use in implantable medical devices is generally disclosed in U.S. Pat. No. 5,885,471 to Ruben, et al., entitled "Shock resistant accelerometer for implantable medical device," filed on Jul. 31, 1997 and issued on Mar. 23, 1999, the entire content of which is incorporated herein by reference. Additional detail with respect to an implantable medical device arrangement including a piezoelectric accelerometer for detecting patient motion is set forth in U.S. Pat. No. 4,485,813 to Anderson, et al., entitled "Implantable dynamic pressure transducer system," filed on Nov. 19, 1981, and issued on Dec. 4, 1984, and U.S. Pat. No. 5,052,388 to Sivula, et al., entitled "Method and apparatus for implementing activity sensing in a pulse generator," filed on Dec. 22, 1989, and issued on Oct. 1, 1991, the entire contents of each of which is incorporated by reference herein. Examples of three-dimensional accelerometers that may be implemented in pacemaker 10 and used for detecting cardiac mechanical events is set forth in in U.S. Pat. No. 5,593,431 to Sheldon, entitled "Medical service employing multiple DC accelerometers for patient activity and posture sensing and method," filed on Mar. 30, 1995 and issued on Jan. 14, 1997, and U.S. Pat. No. 6,044,297 to Sheldon, entitled "Posture and device orientation and calibration for implantable medical devices," filed on Sep. 25, 1998, and issued on Mar. 28, 2000, the entire contents of each of which are incorporated herein by reference. Other accelerometer designs may be used for producing an electrical signal that is correlated to motion imparted on pacemaker 10 due to ventricular and atrial events.

The various circuits represented in FIG. 4 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality.

Sensing circuit 204 is configured to sense electrogram data by sensing a cardiac electrical signal via electrodes 162 and 164 by a pre-filter and amplifier circuit 220. Pre-filter and amplifier circuit 220 may include a high pass filter to remove DC offset, e.g., a 2.5 to 5 Hz high pass filter, or a wideband filter having a passband of 2.5 Hz to 100 Hz to remove DC offset and high frequency noise. Pre-filter and amplifier circuit 220 may further include an amplifier to amplify the "raw" cardiac electrical signal passed to rectifier and amplifier circuit 222 and analog-to-digital converter (ADC) 226. ADC 226 may pass a multi-bit, digital electrogram (EGM) signal to control circuit 206 for use, in some cases, by atrial event detector circuit 240 for detecting atrial electrical events, such as P-waves. For example, atrial event detector circuit 240 may use identification of atrial electrical events in algorithms for detecting atrial systolic events from the mechanical motion signal provided by motion sensor 212. The amplified signal of pre-filter and amplifier circuit 220 may also be passed to rectifier and amplifier circuit 222, which may include a rectifier, bandpass filter, and amplifier for passing a cardiac signal to ventricular event detector circuit 224 for use in identifying ventricular electrical events (e.g., R-waves or T-waves).

Ventricular event detector circuit 224 may include a sense amplifier or other detection circuitry that compares the incoming rectified, cardiac electrical signal to a ventricular event detection threshold, which may be an auto-adjusting threshold. In some examples, ventricular event detector circuit 224 is configured to detect ventricular events, such as an R-wave or a T-wave. When the incoming signal crosses the ventricular event detection threshold, ventricular event detector circuit 224 produces a sensed ventricular event signal (e.g., which may be an R-sense signal where an R-wave is detected) that is passed to control circuit 206. In other examples not expressly depicted in the example of FIG. 3, ventricular event detector circuit 224 may be configured to receive a digital output of ADC 226 for detecting ventricular events by a comparator, morphological signal analysis of the digital EGM signal, or to perform other ventricular event detection techniques. Sensed ventricular event signals passed from ventricular event detector circuit 224 to control circuit 206 may be used for scheduling ventricular pacing pulses by pace timing circuit 242 and for use in identifying the timing of ventricular electrical events in algorithms performed by atrial event detector circuit 240 for detecting atrial systolic events from a signal received from motion sensor 212.

Control circuit 206 includes an atrial event detector circuit 240, pace timing circuit 242, and processing circuitry 244. Atrial event detector circuit 240 is configured to detect atrial mechanical events from a signal received from motion sensor 212. In some examples, one or more ventricular mechanical events may be detected from the motion sensor signal in a given cardiac cycle to facilitate positive detection of the atrial systolic event from the motion sensor signal during the ventricular cycle.

Control circuit 206 may receive sensed ventricular event signals, such as sensed R-wave events, and/or digital electrogram data from sensing circuit 204 for use in detecting and confirming cardiac events and controlling ventricular pacing. For example, R-wave sensed event signals may be passed to pace timing circuit 242 for inhibiting scheduled ventricular pacing pulses or scheduling ventricular pacing pulses when pacemaker 10 is operating in a non-atrial tracking (asynchronous) ventricular pacing mode. R-wave sensed event signals may also be passed to atrial event detector circuit 240 for use in setting time windows used by control circuit 206 for detecting atrial systolic events from the motion sensor signal.

Atrial event detector circuit 240 receives a mechanical motion signal from motion sensor 212 and may start an atrial refractory period in response to a ventricular electrical event, e.g., an R-wave sensed event signal from sensing circuit 204 or delivery of a ventricular pacing pulse by pulse generation circuit 202. In some examples, atrial event detector circuit 240 determines if the motion sensor signal satisfies atrial mechanical event detection criteria outside of the refractory period. The motion sensor signal during the refractory period may be monitored by atrial event detector circuit 240 for the purposes of detecting ventricular mechanical events, which may be used for confirming or validating atrial systolic event detection. As such, ventricular mechanical event detection windows may be set during the atrial refractory period and may be set according to predetermined time intervals following identification of a ventricular electrical event.

Pace timing circuit 242 (or processing circuitry 244) may additionally receive sensed ventricular event signals, such as sensed R-wave event signals, from ventricular event detector circuit 224 for use in controlling the timing of pacing pulses delivered by pulse generation circuit 202. In some examples, processing circuitry 244 is one or more microprocessors, digital signal processors (DSPs), application specific integrated circuits (ASICs), field programmable gate arrays (FPGAs), or any other equivalent integrated or discrete logic circuitry, as well as any combinations of such components. Processing circuitry 244 may include one or more clocks for generating clock signals that are used by pace timing circuit 242 to time out an AV pacing interval that is started upon receipt of an atrial event detection signal from atrial event detector circuit 240. Pace timing circuit 242 may include one or more pacing escape interval timers or counters that are used to time out the AV pacing interval, which may be a programmable interval stored in memory 210 and retrieved by processing circuitry 244 for use in setting the AV pacing interval used by pace timing circuit 242.

Pace timing circuit 242 may additionally include a lower pacing rate interval timer for controlling a lower ventricular pacing rate. For example, if an atrial systolic event is not detected from the motion sensor signal, thus not initiating the programmed AV pacing interval for triggering a ventricular pacing pulse, a ventricular pacing pulse may nevertheless be delivered by pulse generation circuit 202 upon expiration of the lower pacing rate interval to prevent ventricular asystole and maintain a minimum ventricular rate.

Processing circuitry 244 may retrieve other programmable pacing control parameters, such as pacing pulse amplitude and pacing pulse width, which are passed to pulse generation circuit 202 for controlling pacing pulse delivery from memory 210. In addition to providing control signals to pace timing circuit 242 and pulse generation circuit 202 for controlling pacing pulse delivery, processing circuitry 244 may provide sensing control signals to sensing circuit 204, e.g., ventricular event sensing thresholds such as an R-wave sensing threshold, sensitivity, and/or various blanking and refractory intervals applied to the electrogram data.

Pulse generation circuit 202 generates electrical pacing pulses that are delivered to the RV of the patient's heart via cathode electrode 164 and return anode electrode 162. Pulse generation circuit 202 may include charging circuit 230, switching circuit 232 and an output circuit 234. Charging circuit 230 may include a holding capacitor that may be charged to a pacing pulse amplitude by a multiple of the battery voltage signal of power source 214 under the control of a voltage regulator. The pacing pulse amplitude may be set based on a control signal from control circuit 206. Switching circuit 232 may control when the holding capacitor of charging circuit 230 is coupled to the output circuit 234 for delivering the pacing pulse. For example, switching circuit 232 may include a switch that is activated by a timing signal received from pace timing circuit 242 upon expiration of an AV pacing interval, a VV rate smoothing interval, or VV lower rate pacing interval) and kept closed for a programmed pacing pulse width to enable discharging of the holding capacitor of charging circuit 230. The holding capacitor, previously charged to the pacing pulse voltage amplitude, is discharged across electrodes 162 and 164 through the output capacitor of output circuit 234 for the programmed pacing pulse duration. Additional description of pacing circuitry is set forth in U.S. Pat. No. 5,507,782 to Kieval, et al., entitled "Method and apparatus for dual chamber cardiac pacing," filed on Mar. 17, 1994 and issued on Apr. 16, 1996 and U.S. Pat. No. 8,532,785 to Crutchfield, et al., entitled "Therapy delivery method and system for implantable medical devices," filed on Sep. 26, 2012, and issued on Sep. 10, 2013, the entire contents of each of which are incorporated herein by reference. Such pacing circuitry described by U.S. Pat. Nos. 5,507,782 and 8,532,785 may be implemented in pacemaker 10 for charging a pacing capacitor to a predetermined pacing pulse amplitude under the control of control circuit 206 and delivering a pacing pulse.

Memory 210 may include computer-readable instructions that, when executed by control circuit 206, cause control circuit 206 to perform various functions attributed throughout this disclosure to pacemaker 10. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media.

Memory 210 may store event detection parameters 250, such as timing intervals and other data used by control circuit 206 to control the delivery of pacing pulses by pulse generation circuit 202, e.g., by detecting an atrial systolic event by atrial event detector circuit 240 from the motion sensor signal and controlling the timing of delivery of ventricular pacing pulse delivery by pulse generation circuit 202. Such event detection parameters 250 may include, e.g., a beginning or an ending of a detection window for sensing an A7 event, a beginning or an ending of a detection window for sensing an A4 event, a threshold amplitude for the detection window for sensing the A7 event (e.g., such as a minimum threshold or a maximum threshold), a threshold amplitude for the detection window for sensing the A4 event (e.g., such as a minimum threshold or a maximum threshold), or a boundary separating the window for sensing the A7 event from the window for sensing the A4 event, etc.

Power source 214 provides power to each of the other circuits and components of pacemaker 10 as required. Power source 214 may include one or more energy storage devices, such as one or more rechargeable or non-rechargeable batteries. The connections between power source 214 and other pacemaker circuits and components are not shown in FIG. 4 for the sake of clarity but are to be understood from the general block diagram of FIG. 4. For example power source 214 may provide power to charging circuit 230 for charging a holding capacitor to a pacing voltage amplitude, current to switching circuit 232 and other circuitry included in pulse generation circuit 202 as needed, power to transceiver 209, motion sensor 212, and ADC 226 and other circuitry of sensing circuit 204 as needed as well as memory 210.

Telemetry circuit 208 includes a transceiver 209 and antenna 211 for transferring and receiving data via a radio frequency (RF) communication link. Telemetry circuit 208 may be capable of bi-directional communication with computing device 12 (FIG. 1) as described above. Mechanical motion data and electrogram data may be transmitted by telemetry circuit 208 to computing device 12. Furthermore, event detection parameters, pacing control parameters, and algorithms for performing atrial event detection and/or ventricular pacing control may be received by telemetry circuit 208 and stored in memory 210 for access by control circuit 206.

Figure 5:
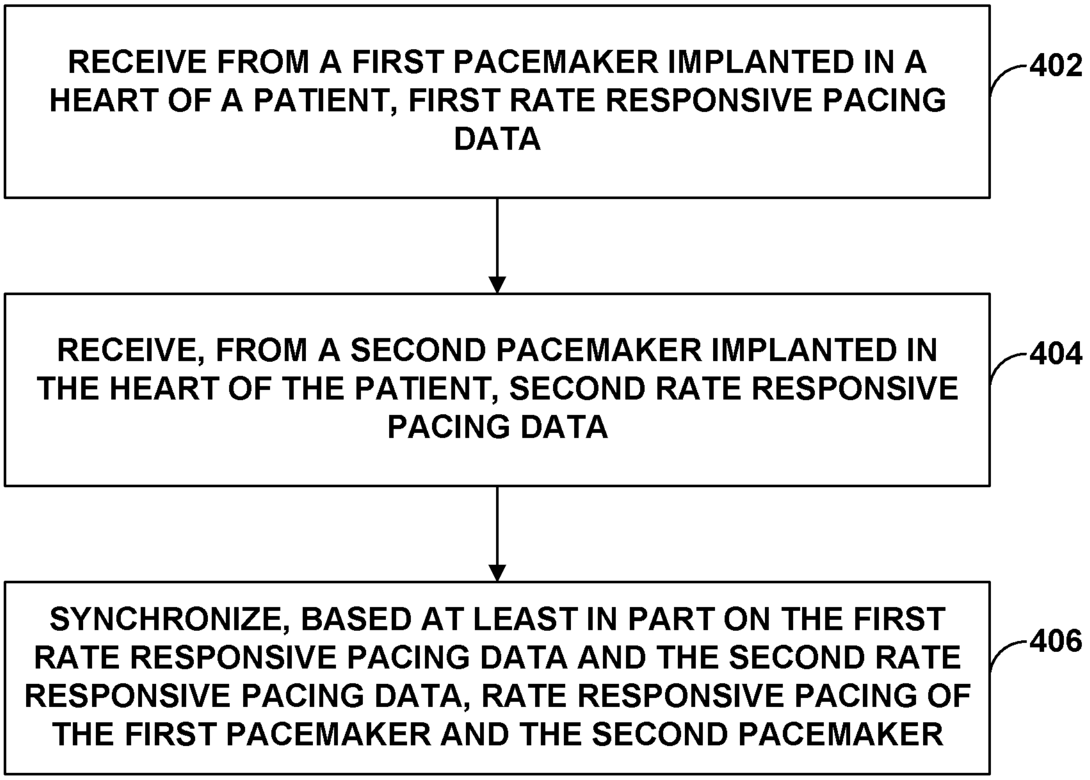
FIG. 5 is a flowchart illustrating an example operation in accordance with the techniques of the disclosure.

FIG. 5 is a flowchart illustrating an example operation in accordance with the techniques of the disclosure. For convenience, FIG. 5 is described with respect to FIGS. 1-4.

As depicted in FIG. 5, processing circuitry 20 of computing device 12 and/or processing circuitry 50 of pacemaker 10 may receive one or more sensor values indicative of motion of a patient 4 (402). For example, processing circuitry 20 may receive accelerometer data from an accelerometer 36 or from any other one or more sensors 32 for sensing motion. Similarly, processing circuitry 50 may receive accelerometer data from an accelerometer 59 or from any other one or more sensors 58 for sensing motion.

Processing circuitry 20 of computing device 12 may receive, from a first pacemaker 10A implanted in a heart 6 of a patient 4, first rate responsive pacing data (404). Processing circuitry 20 may receive, from a second pacemaker 10B implanted in the heart 6 of the patient 4, second rate responsive pacing data (404). Processing circuitry 20 may synchronize, based at least in part on the first rate responsive pacing data and the second rate responsive pacing data, rate responsive pacing of the first pacemaker 10A and the second pacemaker 10B (406).

In some examples, the techniques of the disclosure include a system that comprises means to perform any method described herein. In some examples, the techniques of the disclosure include a computer-readable medium comprising instructions that cause processing circuitry to perform any method described herein.

The techniques of this disclosure includes the following examples.

Example 1: A method includes receiving, by processing circuitry from a first pacemaker implanted in a heart of a patient, first rate responsive pacing data; receiving, by the processing circuitry from a second pacemaker implanted in the heart of the patient, second rate responsive pacing data; and synchronizing, by the processing circuitry and based at least in part on the first rate responsive pacing data and the second rate responsive pacing data, rate responsive pacing of the first pacemaker and the second pacemaker.

Example 2: The method of example 1, wherein: the first rate responsive pacing data is collected by the first pacemaker as the patient undergoes a triggered exercise test; and the second rate responsive pacing data is collected by the second pacemaker as the patient undergoes the triggered exercise test.

Example 3: The method of example 2, wherein the triggered exercise test includes at least a period of rest for the patient and a period of moderate exercise for the triggered exercise test.

Example 4: The method of any of examples 2 and 3, wherein: the first rate responsive pacing data includes first activity counts generated by the first pacemaker during the triggered exercise test based at least in part on a first accelerometer data generated by a first activity sensor of the first pacemaker and a first activity counts algorithm; the second rate responsive pacing data includes second activity counts generated by the second pacemaker during the triggered exercise test based at least in part on a second accelerometer data generated by a second activity sensor of the second pacemaker and a second activity counts algorithm; and synchronizing the rate responsive pacing of the first pacemaker with the rate responsive pacing of the second pacemaker further comprises modifying, by the processing circuitry, at least one of: the first activity counts algorithm of the first pacemaker or one or more parameters of the first activity sensor such that the first pacemaker is able to generate, from the first rate responsive pacing data, first activity counts that match the second activity counts generated by the second pacemaker during the triggered exercise test.

Example 5: The method of example 4, wherein modifying at least one of: the first activity counts algorithm of the first pacemaker or the one or more parameters of the first activity sensor further comprises: programming, by the processing circuitry, the first pacemaker to modify at least one of: associations between activity counts and pacing rates of the first pacemaker or the one or more parameters of the first activity sensor.

Example 6: The method of any of examples 2-5, wherein: the first rate responsive pacing data includes first activity counts generated by the first pacemaker during the triggered exercise test based at least in part on first accelerometer data generated by a first activity sensor of the first pacemaker and a first rate response slope; the second rate responsive pacing data includes second activity counts generated by the second pacemaker during the triggered exercise test based at least in part on second accelerometer data generated by a second activity sensor of the second pacemaker and a second rate response slope; and synchronizing the rate responsive pacing of the first pacemaker with the rate responsive pacing of the second pacemaker further comprises modifying associations between the first activity counts and pacing rates of the first pacemaker to modify the first rate response slope of the first pacemaker to match the second rate response slope of the second pacemaker.

Example 7: The method of any of examples 2-5, wherein: the first rate responsive pacing data includes first activity counts generated by the first pacemaker during the triggered exercise test based at least in part on first accelerometer data generated by a first activity sensor of the first pacemaker and a first rate response slope associated with first associations between activity counts and pacing rates of the first pacemaker; the second rate responsive pacing data includes second activity counts generated by the second pacemaker during the triggered exercise test based at least in part on second accelerometer data generated by a second activity sensor of the second pacemaker and a second rate response slope generated associated with second associations between activity counts and pacing rates of the second pacemaker; and synchronizing the rate responsive pacing of the first pacemaker with the rate responsive pacing of the second pacemaker further comprises modifying, by the processing circuitry, the first associations between activity counts and pacing rates of the first pacemaker and the second associations between activity counts and pacing rates of the second pacemaker, such that each of the first pacemaker and the second pacemaker is able to achieve a specified target pacing rate given a specified activity level of the patient.

Example 8: The method of any of examples 1 through 7, wherein the first rate responsive pacing data is collected by the first pacemaker over a period of time since a last follow-up clinical visit by the patient; and the second rate responsive pacing data is collected by the second pacemaker over the period of time since the last follow-up clinical visit by the patient.

Example 9: The method of example 8, wherein: the first rate responsive pacing data includes first pacing rate data and activity counts generated by the first pacemaker; the second rate responsive pacing data includes second pacing rate data; and synchronizing the rate responsive pacing of the first pacemaker with the rate responsive pacing of the second pacemaker further comprises: generating, by the processing circuitry, a first sensor rate histogram based at least in part on the first pacing rate data; generating, by the processing circuitry, a second sensor rate histogram based at least in part on the second pacing rate data; and determining, by the processing circuitry, a rate response algorithm for the first pacemaker, such that the rate response algorithm is usable to generate, based on the activity counts, pacing rate data having a sensor rate histogram that matches the second sensor rate histogram.

Example 10: The method of any of examples 8 and 9, wherein: the first rate responsive pacing data includes first pacing rate data and first activity counts generated by the first pacemaker; the second rate responsive pacing data includes second activity counts generated by the second pacemaker; and synchronizing the rate responsive pacing of the first pacemaker with the rate responsive pacing of the second pacemaker further comprises: generating, by the processing circuitry, a first activity counts histogram based at least in part on the first pacing rate data; generating, by the processing circuitry, a second activity counts histogram based at least in part on the second pacing rate data; and determining, by the processing circuitry, a rate response algorithm for the first pacemaker, such that the rate response algorithm is usable to generate pacing rate data having an activity count histogram that matches the second activity counts histogram.

Example 11: The method of any of examples 9 and 10, wherein synchronizing the rate responsive pacing of the first pacemaker with the rate responsive pacing of the second pacemaker further comprises: programming, by the processing circuitry, the first pacemaker to use the rate responsive algorithm for pacing the patient.

Example 12: The method of any of examples 1-11, wherein the first pacemaker is disposed in an atrium of the heart of the patient, and wherein the second pacemaker is disposed in a ventricle of the heart of the patient.

Example 13: A medical device includes memory; and processing circuitry operably coupled to the memory and configured to: receive, from a first pacemaker implanted in a heart of a patient, first rate responsive pacing data; receive, from a second pacemaker implanted in the heart of the patient, second rate responsive pacing data; and synchronize, based at least in part on the first rate responsive pacing data and the second rate responsive pacing data, rate responsive pacing of the first pacemaker and the second pacemaker.

Example 14: The medical device of example 13, wherein: the first rate responsive pacing data is collected by the first pacemaker as the patient undergoes a triggered exercise test; and the second rate responsive pacing data is collected by the second pacemaker as the patient undergoes the triggered exercise test.

Example 15: The medical device of example 14, wherein the triggered exercise test includes at least a period of rest for the patient and a period of moderate exercise for the triggered exercise test.

Example 16: The medical device of any of examples 14 and 15, wherein: the first rate responsive pacing data includes first activity counts generated by the first pacemaker during the triggered exercise test based at least in part on a first accelerometer data generated by a first activity sensor of the first pacemaker and a first activity counts algorithm; the second rate responsive pacing data includes second activity counts generated by the second pacemaker during the triggered exercise test based at least in part on a second accelerometer data generated by a second activity sensor of the second pacemaker and a second activity counts algorithm; and to synchronize the rate responsive pacing of the first pacemaker with the rate responsive pacing of the second pacemaker, the processing circuitry is further configured to modify at least one of: the first activity counts algorithm of the first pacemaker or one or more parameters of the first activity sensor such that the first pacemaker is able to generate, from the first rate responsive pacing data, first activity counts that match the second activity counts generated by the second pacemaker during the triggered exercise test.

Example 17: The medical device of example 16, wherein to modify at least one of: the first activity counts algorithm of the first pacemaker or the one or more parameters of the first activity sensor, the processing circuitry is further configured to: program the first pacemaker to modify at least one of: associations between activity counts and pacing rates of the first pacemaker or the one or more parameters of the first activity sensor.

Example 18: The medical device of any of examples 14-17, wherein: the first rate responsive pacing data includes first activity counts generated by the first pacemaker during the triggered exercise test based at least in part on first accelerometer data generated by a first activity sensor of the first pacemaker and a first rate response slope; the second rate responsive pacing data includes second activity counts generated by the second pacemaker during the triggered exercise test based at least in part on second accelerometer data generated by a second activity sensor of the second pacemaker and a second rate response slope; and to synchronize the rate responsive pacing of the first pacemaker with the rate responsive pacing of the second pacemaker, the processing circuitry is further configured to modify associations between the first activity counts and pacing rates of the first pacemaker to modify the first rate response slope of the first pacemaker to match the second rate response slope of the second pacemaker.

Example 19: The medical device of any of examples 14-17, wherein: the first rate responsive pacing data includes first activity counts generated by the first pacemaker during the triggered exercise test based at least in part on first accelerometer data generated by a first activity sensor of the first pacemaker and a first rate response slope associated with first associations between activity counts and pacing rates of the first pacemaker; the second rate responsive pacing data includes second activity counts generated by the second pacemaker during the triggered exercise test based at least in part on second accelerometer data generated by a second activity sensor of the second pacemaker and a second rate response slope generated associated with second associations between activity counts and pacing rates of the second pacemaker; and to synchronize the rate responsive pacing of the first pacemaker with the rate responsive pacing of the second pacemaker, the processing circuitry is further configured to modify the first associations between activity counts and pacing rates of the first pacemaker and the second associations between activity counts and pacing rates of the second pacemaker, such that each of the first pacemaker and the second pacemaker is able to achieve a specified target pacing rate given a specified activity level of the patient.

Example 20: The medical device of any of examples 13 through 19, wherein the first rate responsive pacing data is collected by the first pacemaker over a period of time since a last follow-up clinical visit by the patient; and the second rate responsive pacing data is collected by the second pacemaker over the period of time since the last follow-up clinical visit by the patient.

Example 21: The medical device of example 20, wherein: the first rate responsive pacing data includes first pacing rate data and activity counts generated by the first pacemaker; the second rate responsive pacing data includes second pacing rate data; and to synchronize the rate responsive pacing of the first pacemaker with the rate responsive pacing of the second pacemaker, the processing circuitry is further configured to: generate a first sensor rate histogram based at least in part on the first pacing rate data; generate a second sensor rate histogram based at least in part on the second pacing rate data; and determine a rate response algorithm for the first pacemaker, such that the rate response algorithm is usable to generate, based on the activity counts, pacing rate data having a sensor rate histogram that matches the second sensor rate histogram.

Example 22: The medical device of any of examples 20 and 21, wherein: the first rate responsive pacing data includes first pacing rate data and first activity counts generated by the first pacemaker; the second rate responsive pacing data includes second activity counts generated by the second pacemaker; and to synchronize the rate responsive pacing of the first pacemaker with the rate responsive pacing of the second pacemaker, the processing circuitry is further configured to: generate a first activity counts histogram based at least in part on the first pacing rate data; generate a second activity counts histogram based at least in part on the second pacing rate data; and determine a rate response algorithm for the first pacemaker, such that the rate response algorithm is usable to generate pacing rate data having an activity count histogram that matches the second activity counts histogram.

Example 23: The medical device of any of examples 21 and 22, wherein to synchronize the rate responsive pacing of the first pacemaker with the rate responsive pacing of the second pacemaker, the processing circuitry is further configured to: program the first pacemaker to use the rate responsive algorithm for pacing the patient.

Example 24: The medical device of any of examples 13-23, wherein the first pacemaker is disposed in an atrium of the heart of the patient, and wherein the second pacemaker is disposed in a ventricle of the heart of the patient.

Example 25: A non-transitory computer-readable medium includes receive, from a first pacemaker implanted in a heart of a patient, first rate responsive pacing data; receive, from a second pacemaker implanted in the heart of the patient, second rate responsive pacing data; and synchronize, based at least in part on the first rate responsive pacing data and the second rate responsive pacing data, rate responsive pacing of the first pacemaker and the second pacemaker.

Example 26: A non-transitory computer-readable medium comprising instructions that, when executed by processing circuitry of a medical device, cause the medical device to perform any of the methods of examples 1-12.

Example 27: An apparatus includes means for receiving, from a first pacemaker implanted in a heart of a patient, first rate responsive pacing data; means for receiving, from a second pacemaker implanted in the heart of the patient, second rate responsive pacing data; and means for synchronizing, based at least in part on the first rate responsive pacing data and the second rate responsive pacing data, rate responsive pacing of the first pacemaker and the second pacemaker.

Example 28: An apparatus comprising means for performing any of the methods of examples 1-12.

Example 29: A medical device includes memory; and processing circuitry operably coupled to the memory and configured to perform any of the methods of claims 1-12.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module, unit, or circuit for purposes of clarity, it should be understood that the techniques of this disclosure may be performed by a combination of units, modules, or circuitry associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing circuitry" as used herein may refer to any of the foregoing structure or any other physical structure suitable for implementation of the described techniques. Also, the techniques could be fully implemented in one or more circuits or logic elements.

Various examples have been described. These and other examples are within the scope of the following claims.

What is claimed is:

1. A method comprising:

receiving, by processing circuitry of a computing device and from a first pacemaker implanted in a heart of a patient, first rate responsive pacing data;

receiving, by the processing circuitry and from a second pacemaker implanted in the heart of the patient, second rate responsive pacing data; and synchronizing, by the processing circuitry and based at least in part on the first rate responsive pacing data and the second rate responsive pacing data, rate responsive pacing of the first pacemaker and the second pacemaker.

2. The method of claim 1, wherein:

the first rate responsive pacing data is collected by the first pacemaker as the patient undergoes a triggered exercise test; and the second rate responsive pacing data is collected by the second pacemaker as the patient undergoes the triggered exercise test.

3. The method of claim 2, wherein:

the first rate responsive pacing data includes first activity counts generated by the first pacemaker during the triggered exercise test based at least in part on a first accelerometer data generated by a first activity sensor of the first pacemaker and a first activity counts algorithm;

the second rate responsive pacing data includes second activity counts generated by the second pacemaker during the triggered exercise test based at least in part on a second accelerometer data generated by a second activity sensor of the second pacemaker and a second activity counts algorithm; and synchronizing the rate responsive pacing of the first pacemaker with the rate responsive pacing of the second pacemaker further comprises modifying, by the processing circuitry, at least one of: the first activity counts algorithm of the first pacemaker or one or more parameters of the first activity sensor such that the first pacemaker is able to generate, from the first rate responsive pacing data, first activity counts that match the second activity counts generated by the second pacemaker during the triggered exercise test.

4. The method of claim 3, wherein modifying at least one of: the first activity counts algorithm of the first pacemaker or the one or more parameters of the first activity sensor further comprises:

programming, by the processing circuitry, the first pacemaker to modify at least one of: associations between activity counts and pacing rates of the first pacemaker or the one or more parameters of the first activity sensor.

5. The method of claim 2, wherein:

the first rate responsive pacing data includes first activity counts generated by the first pacemaker during the triggered exercise test based at least in part on first accelerometer data generated by a first activity sensor of the first pacemaker and a first rate response slope;

the second rate responsive pacing data includes second activity counts generated by the second pacemaker during the triggered exercise test based at least in part on second accelerometer data generated by a second activity sensor of the second pacemaker and a second rate response slope; and synchronizing the rate responsive pacing of the first pacemaker with the rate responsive pacing of the second pacemaker further comprises modifying associations between the first activity counts and pacing rates of the first pacemaker to modify the first rate response slope of the first pacemaker to match the second rate response slope of the second pacemaker.

6. The method of claim 2, wherein:

the first rate responsive pacing data includes first activity counts generated by the first pacemaker during the triggered exercise test based at least in part on first accelerometer data generated by a first activity sensor of the first pacemaker and a first rate response slope associated with first associations between activity counts and pacing rates of the first pacemaker;

the second rate responsive pacing data includes second activity counts generated by the second pacemaker during the triggered exercise test based at least in part on second accelerometer data generated by a second activity sensor of the second pacemaker and a second rate response slope generated associated with second associations between activity counts and pacing rates of the second pacemaker; and synchronizing the rate responsive pacing of the first pacemaker with the rate responsive pacing of the second pacemaker further comprises modifying, by the processing circuitry, the first associations between activity counts and pacing rates of the first pacemaker and the second associations between activity counts and pacing rates of the second pacemaker, such that each of the first pacemaker and the second pacemaker is able to achieve a specified target pacing rate given a specified activity level of the patient.

7. The method of claim 1, wherein the first rate responsive pacing data is collected by the first pacemaker over a period of time since a last follow-up clinical visit by the patient; and the second rate responsive pacing data is collected by the second pacemaker over the period of time since the last follow-up clinical visit by the patient.

8. The method of claim 7, wherein:

the first rate responsive pacing data includes first pacing rate data and activity counts generated by the first pacemaker;

the second rate responsive pacing data includes second pacing rate data; and synchronizing the rate responsive pacing of the first pacemaker with the rate responsive pacing of the second pacemaker further comprises:

generating, by the processing circuitry, a first sensor rate histogram based at least in part on the first pacing rate data;

generating, by the processing circuitry, a second sensor rate histogram based at least in part on the second pacing rate data; and determining, by the processing circuitry, a rate response algorithm for the first pacemaker, such that the rate response algorithm is usable to generate, based on the activity counts, pacing rate data having a sensor rate histogram that matches the second sensor rate histogram.

9. The method of claim 7, wherein:

the first rate responsive pacing data includes first pacing rate data and first activity counts generated by the first pacemaker;

the second rate responsive pacing data includes second activity counts generated by the second pacemaker; and synchronizing the rate responsive pacing of the first pacemaker with the rate responsive pacing of the second pacemaker further comprises:

generating, by the processing circuitry, a first activity counts histogram based at least in part on the first pacing rate data;

generating, by the processing circuitry, a second activity counts histogram based at least in part on the second pacing rate data; and determining, by the processing circuitry, a rate response algorithm for the first pacemaker, such that the rate response algorithm is usable to generate pacing rate data having an activity count histogram that matches the second activity counts histogram.

10. The method of claim 8, wherein synchronizing the rate responsive pacing of the first pacemaker with the rate responsive pacing of the second pacemaker further comprises:

programming, by the processing circuitry, the first pacemaker to use the rate responsive algorithm for pacing the patient.

11. A medical device comprising:

memory; and processing circuitry operably coupled to the memory and configured to:

receive, from a first pacemaker implanted in a heart of a patient, first rate responsive pacing data;

receive, from a second pacemaker implanted in the heart of the patient, second rate responsive pacing data; and synchronize, based at least in part on the first rate responsive pacing data and the second rate responsive pacing data, rate responsive pacing of the first pacemaker and the second pacemaker.

12. The medical device of claim 11, wherein:

the first rate responsive pacing data is collected by the first pacemaker as the patient undergoes a triggered exercise test; and the second rate responsive pacing data is collected by the second pacemaker as the patient undergoes the triggered exercise test.

13. The medical device of claim 12, wherein:

the first rate responsive pacing data includes first activity counts generated by the first pacemaker during the triggered exercise test based at least in part on a first accelerometer data generated by a first activity sensor of the first pacemaker and a first activity counts algorithm;

the second rate responsive pacing data includes second activity counts generated by the second pacemaker during the triggered exercise test based at least in part on a second accelerometer data generated by a second activity sensor of the second pacemaker and a second activity counts algorithm; and to synchronize the rate responsive pacing of the first pacemaker with the rate responsive pacing of the second pacemaker, the processing circuitry is further configured to modify at least one of: the first activity counts algorithm of the first pacemaker or one or more parameters of the first activity sensor such that the first pacemaker is able to generate, from the first rate responsive pacing data, first activity counts that match the second activity counts generated by the second pacemaker during the triggered exercise test.

14. The medical device of claim 13, wherein to modify at least one of: the first activity counts algorithm of the first pacemaker or the one or more parameters of the first activity sensor, the processing circuitry is further configured to:

program the first pacemaker to modify at least one of: associations between activity counts and pacing rates of the first pacemaker or the one or more parameters of the first activity sensor.

15. The medical device of claim 12, wherein:

the first rate responsive pacing data includes first activity counts generated by the first pacemaker during the triggered exercise test based at least in part on first accelerometer data generated by a first activity sensor of the first pacemaker and a first rate response slope;

the second rate responsive pacing data includes second activity counts generated by the second pacemaker during the triggered exercise test based at least in part on second accelerometer data generated by a second activity sensor of the second pacemaker and a second rate response slope; and to synchronize the rate responsive pacing of the first pacemaker with the rate responsive pacing of the second pacemaker, the processing circuitry is further configured to modify associations between the first activity counts and pacing rates of the first pacemaker to modify the first rate response slope of the first pacemaker to match the second rate response slope of the second pacemaker.

16. The medical device of claim 12, wherein:

the first rate responsive pacing data includes first activity counts generated by the first pacemaker during the triggered exercise test based at least in part on first accelerometer data generated by a first activity sensor of the first pacemaker and a first rate response slope associated with first associations between activity counts and pacing rates of the first pacemaker;

the second rate responsive pacing data includes second activity counts generated by the second pacemaker during the triggered exercise test based at least in part on second accelerometer data generated by a second activity sensor of the second pacemaker and a second rate response slope generated associated with second associations between activity counts and pacing rates of the second pacemaker; and to synchronize the rate responsive pacing of the first pacemaker with the rate responsive pacing of the second pacemaker, the processing circuitry is further configured to modify the first associations between activity counts and pacing rates of the first pacemaker and the second associations between activity counts and pacing rates of the second pacemaker, such that each of the first pacemaker and the second pacemaker is able to achieve a specified target pacing rate given a specified activity level of the patient.

17. The medical device of claim 11, wherein the first rate responsive pacing data is collected by the first pacemaker over a period of time since a last follow-up clinical visit by the patient; and the second rate responsive pacing data is collected by the second pacemaker over the period of time since the last follow-up clinical visit by the patient.

18. The medical device of claim 17, wherein:

the first rate responsive pacing data includes first pacing rate data and activity counts generated by the first pacemaker;

the second rate responsive pacing data includes second pacing rate data; and to synchronize the rate responsive pacing of the first pacemaker with the rate responsive pacing of the second pacemaker, the processing circuitry is further configured to:

generate a first sensor rate histogram based at least in part on the first pacing rate data;

generate a second sensor rate histogram based at least in part on the second pacing rate data; and determine a rate response algorithm for the first pacemaker, such that the rate response algorithm is usable to generate, based on the activity counts, pacing rate data having a sensor rate histogram that matches the second sensor rate histogram.

19. The medical device of claim 17, wherein:

the first rate responsive pacing data includes first pacing rate data and first activity counts generated by the first pacemaker;

the second rate responsive pacing data includes second activity counts generated by the second pacemaker; and to synchronize the rate responsive pacing of the first pacemaker with the rate responsive pacing of the second pacemaker, the processing circuitry is further configured to:

generate a first activity counts histogram based at least in part on the first pacing rate data;

generate a second activity counts histogram based at least in part on the second pacing rate data; and determine a rate response algorithm for the first pacemaker, such that the rate response algorithm is usable to generate pacing rate data having an activity count histogram that matches the second activity counts histogram.

20. A non-transitory computer-readable medium comprising instructions that, when executed by processing circuitry of a medical device, cause the medical device to:

receive, from a first pacemaker implanted in a heart of a patient, first rate responsive pacing data;

receive, from a second pacemaker implanted in the heart of the patient, second rate responsive pacing data; and synchronize, based at least in part on the first rate responsive pacing data and the second rate responsive pacing data, rate responsive pacing of the first pacemaker and the second pacemaker.

* * * * *